(12) United States Patent
Hockaday

(10) Patent No.: US 11,229,197 B2
(45) Date of Patent: Jan. 25, 2022

(54) ARTHROPOD REPELLENT OR ATTRACTANT LIQUID RESERVOIR WITH FILL INDICATOR

(71) Applicant: Energy Related Devices, Inc., Tucumcari, NM (US)

(72) Inventor: Robert G. Hockaday, Los Alamos, NM (US)

(73) Assignee: Energy Related Devices, Inc., Tucumcari, NM (US)

( * ) Notice: Subject to any disclaimer, the term of this patent is extended or adjusted under 35 U.S.C. 154(b) by 205 days.

(21) Appl. No.: 16/086,430

(22) PCT Filed: Mar. 24, 2017

(86) PCT No.: PCT/US2017/023935
§ 371 (c)(1),
(2) Date: Sep. 19, 2018

(87) PCT Pub. No.: WO2017/165721
PCT Pub. Date: Sep. 28, 2017

(65) Prior Publication Data
US 2019/0090469 A1    Mar. 28, 2019

Related U.S. Application Data

(60) Provisional application No. 62/312,498, filed on Mar. 24, 2016.

(51) Int. Cl.
*A01M 1/02* (2006.01)
*A01M 29/12* (2011.01)
(Continued)

(52) U.S. Cl.
CPC ............ *A01M 1/02* (2013.01); *A01M 1/2027* (2013.01); *A01M 1/2044* (2013.01);
(Continued)

(58) Field of Classification Search
CPC . A61L 9/01; A61L 9/042; A61L 9/046; A61L 9/127; A61L 9/12; A01M 1/02;
(Continued)

(56) References Cited

U.S. PATENT DOCUMENTS 4,020,156 A * 4/1977 Murray ................ A61K 8/0241
424/76.6
4,753,086 A * 6/1988 Schmidt ............... A44C 5/0084
63/3

(Continued)

FOREIGN PATENT DOCUMENTS

| CN | 204015230 U | 12/2014 |
|----|-------------|---------|
| EP | 0194859 A2 | 9/1986 |
| WO | 2005118007 A1 | 12/2005 |

OTHER PUBLICATIONS

Momen and Farzaheh, "Survey of Micro/Nano Filler use to Improve Silicone Rubber for Outdoor Insulators", Rev.Adv. Mater.Sci 27(2011) 1-13.

*Primary Examiner* — Darren W Gorman
(74) *Attorney, Agent, or Firm* — James Creighton Wray

(57) ABSTRACT

A progressive liquid fill capacity indicator located inside a vapor diffusion membrane liquid reservoir that utilizes index refraction matching of liquid contact to components, dyes, and surface tension gradients. This fill capacity indicator is low cost and reliable. It enables users to visually assess readiness and remaining liquid capacity to deliver attraction, masking, and repulsion scent vapors from wearable and stationary devices to repel or attract mosquitos and arthropods.

18 Claims, 19 Drawing Sheets

(51) Int. Cl.
*A61L 9/04* (2006.01)
*A61L 9/12* (2006.01)
*G01F 23/22* (2006.01)
*A01M 1/20* (2006.01)

(52) U.S. Cl.
CPC .............. *A01M 29/12* (2013.01); *A61L 9/042* (2013.01); *A61L 9/046* (2013.01); *A61L 9/127* (2013.01); *G01F 23/22* (2013.01)

(58) Field of Classification Search
CPC .. A01M 1/2027; A01M 1/2044; A01M 29/12; G01F 23/22; A44C 5/0084; A01K 13/003; A01K 27/007
USPC .................................. 239/35; 428/34.9, 690
See application file for complete search history.

(56) References Cited

U.S. PATENT DOCUMENTS

| | | | |
|---|---|---|---|
| 4,889,285 A | 12/1989 | Locko | |
| 5,037,343 A * | 8/1991 | Benites | A63H 3/003 446/268 |
| 5,390,510 A * | 2/1995 | Tirio-Cloonan | A44C 15/002 132/294 |
| 6,326,097 B1 | 12/2001 | Hockaday | |
| 6,357,260 B1 * | 3/2002 | Lutz | A44C 11/002 206/6.1 |
| 6,372,242 B1 * | 4/2002 | Gutierrez | A01N 25/04 424/411 |
| 6,604,297 B2 * | 8/2003 | Hagemann | D06F 58/203 34/331 |
| 6,630,266 B2 | 10/2003 | Hockaday | |
| 6,718,689 B1 | 4/2004 | Kolibas | |
| 6,820,773 B1 * | 11/2004 | Orth | A01M 1/2044 222/187 |
| 7,045,204 B2 * | 5/2006 | Enguchi | A44C 15/002 239/34 |
| 7,067,188 B1 * | 6/2006 | Yang | B29C 70/64 428/327 |
| 7,188,780 B2 * | 3/2007 | Martens, III | A61L 9/04 206/484.1 |
| 7,213,770 B2 * | 5/2007 | Martens, III | A01M 1/2055 206/484.1 |
| 7,440,683 B2 * | 10/2008 | Bankers | A01M 1/2044 392/386 |
| 7,665,238 B2 * | 2/2010 | Majerowski | A01M 1/2055 40/725 |
| 7,708,553 B2 | 5/2010 | Hockaday | |
| 7,892,487 B2 * | 2/2011 | Adair | A01M 1/2077 422/400 |
| 7,917,018 B2 * | 3/2011 | Schumacher | A61L 9/122 392/390 |
| 7,988,984 B2 * | 8/2011 | Hockaday | A01M 1/2061 424/403 |
| 8,048,053 B2 * | 11/2011 | Minoguchi | A61F 13/202 604/385.17 |
| 8,511,580 B2 * | 8/2013 | Caserta | A61L 9/12 239/45 |
| 8,968,647 B2 * | 3/2015 | Fischer | A61L 9/12 422/5 |
| 2002/0016250 A1 | 2/2002 | Hayakawa | |
| 2002/0041860 A1 * | 4/2002 | Requejo | A61L 9/12 424/76.1 |
| 2003/0089791 A1 * | 5/2003 | Chen | A61L 9/048 239/35 |
| 2003/0121418 A1 * | 7/2003 | Loop | B01D 53/261 96/117.5 |
| 2003/0223657 A1 * | 12/2003 | Belias | B65D 31/04 383/105 |
| 2006/0000922 A1 | 1/2006 | Martens | |
| 2008/0056691 A1 * | 3/2008 | Wingo | A61L 9/127 392/395 |
| 2008/0272201 A1 * | 11/2008 | Bankers | A61L 9/048 239/35 |
| 2009/0008411 A1 | 1/2009 | Schumacher | |
| 2009/0269451 A1 * | 10/2009 | Perillo | C12G 3/04 426/250 |
| 2009/0313883 A1 | 12/2009 | Olson | |
| 2010/0001417 A1 * | 1/2010 | D'Amico | A61L 9/03 261/26 |
| 2011/0030233 A1 * | 2/2011 | He | D06F 58/203 34/89 |
| 2012/0214380 A1 * | 8/2012 | Vine, III | A44C 5/0092 446/121 |
| 2014/0061328 A1 * | 3/2014 | Haymond | A61L 9/12 239/6 |
| 2014/0221511 A1 * | 8/2014 | Al-Ghamdi | C08J 9/0061 521/59 |
| 2015/0258236 A1 * | 9/2015 | Muller | A61L 9/127 512/22 |

\* cited by examiner

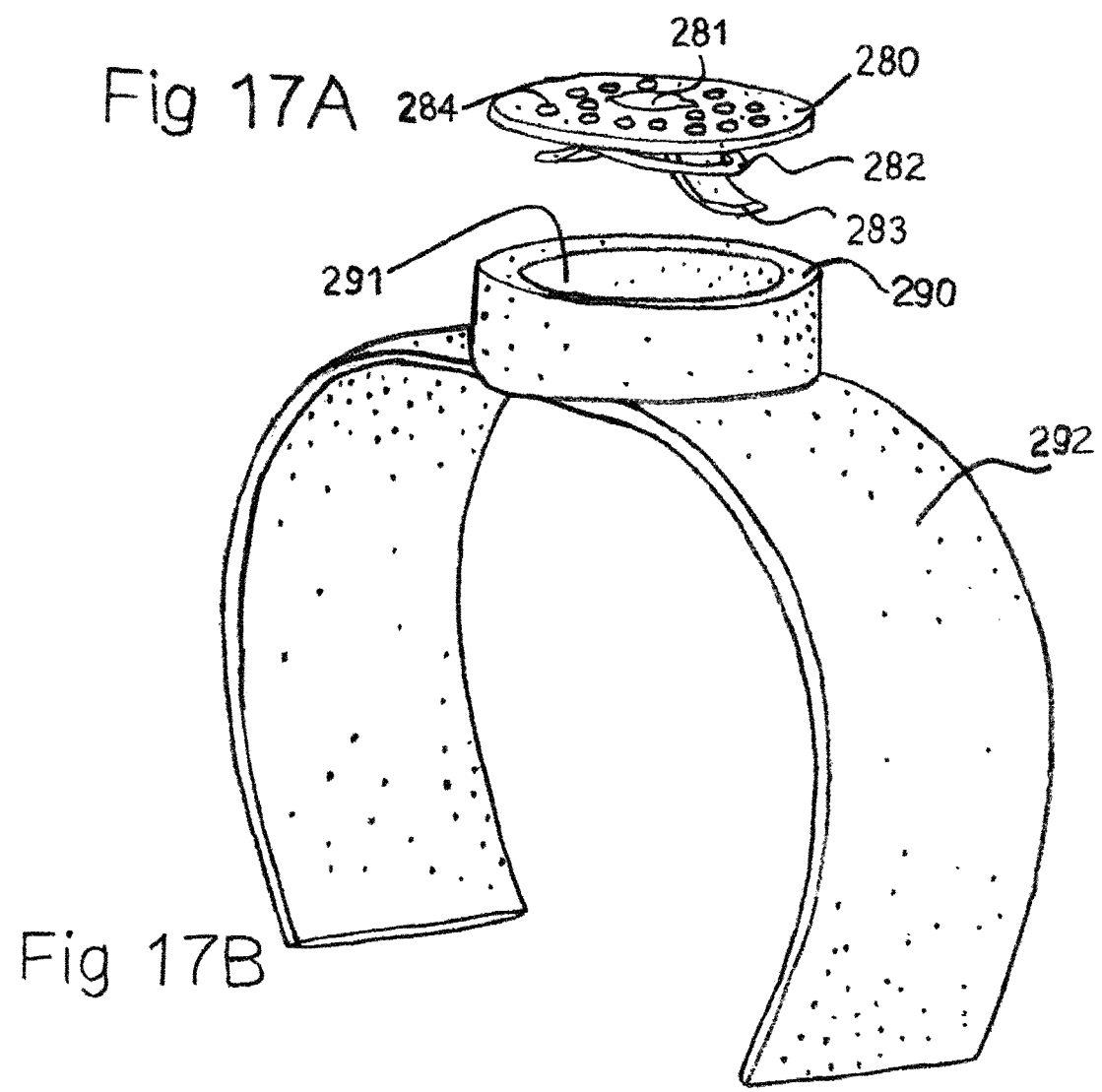

ARTHROPOD REPELLENT OR ATTRACTANT LIQUID RESERVOIR WITH FILL INDICATOR

This application claims the benefit of U.S. Provisional Application No. 62/312,498 filed Mar. 24, 2016 and PCT/US2017/023935 filed Mar. 24, 2017, International Publication No. WO 2017/165721 A1, which are hereby incorporated by reference in their entirety as if fully set forth herein.

BACKGROUND OF INVENTION

Non-skin contact mosquito scent repellent devices that have a reservoir of scent material need a mechanism for the user to know how much scent material is in this reservoir, how much longer it will remain effective, and when it is expended. For the user this mechanism should progressively indicate the amount of scent fill level in the reservoir. Odor emissions are one indicator that the device is operating, but it is not very accurate because the ability of the user to quantitatively gauge the amount is not precise and quantitative. Mosquito affective scents may also not have a strong odor to human senses while an indicator fragrance may be added which is more volatile. The complex ingredients in the scent liquids used may often diffuse at different rates leading to the situation where the more fragrant scent components diffuse out more quickly while the device is still delivering an effective repellent scent, but the mosquito affective scent is undetectable. The human olfactory system is complex and is overlaid with the brain processing to ignore scents after initial detection. The surface emissions may also not be a direct correlation of the reservoir capacity. Indirect methods of timers or parallel diffusion color changes are indirect and parallel means of estimating fill levels of the reservoir. It is most desirable to have a direct clear indicator of the scent reservoir quantity. It is also desirable that the indicator be as inexpensive as possible to enable the product to be used most widely in a variety of environmental conditions of temperature and relative humidities. Fuel level indicator systems in the past have been described in our own patent (U.S. Pat. Nos. 6,326,097, 6,630,266) for fuel cell systems. For small wearable mosquito products the quantities of material are in milliliters and the scents are generally oils, but may have a range of other ingredients including water, salts, surfactants, and alcohols. In our U.S. Pat. No. 7,988,984 a diffusion ampoule to deliver mosquito repellents and attractants contained hydrating salts to take up or release water depending on temperatures, but they were not a repeatable indicator of fluid level as the scent liquids are removed. Typically, as the salt crystals are dried the dimensions of the crystals change depending on the crystallization conditions. They often form larger grains from the fine powders that were originally loaded into the ampoule, and because of their higher density in the scent liquid, they can separate from the liquid. In our U.S. Pat. No. 7,988,984 tubular ampoules were described and the problem with viewing scent liquid fluids in tubes and small ampoules is that most of them have little transmission or reflection contrast between gas or liquid within these small transparent containers so direct sighting of the liquid level can be difficult and ambiguous. Dyes can be added that make the liquid to gas interface more visible but they can stain outside surfaces if the product is broken. Dyes can also be an added complication for refilling and quality control of the product, particularly if the product is repetitively refilled. The dye can leave deposits or progressively become darker. The dyes can be poisonous which is unacceptable for consumer products. Viewing the entire scent ampoule to assess where the liquid is may not be practical in some packaged products. So it is desirable to be able to assess the remaining liquid by only viewing a portion of the scent liquid ampoule.

PRIOR ART

Hockaday U.S. Pat. No. 6,630,266 "Diffusion Fuel Ampoules for Fuel Cells" describes permeable membrane ampoules to deliver fuel to fuel cells. Hockaday describes viewing windows to the fuel ampoule, color stripes and adding dyes and salts to the fuel. The dyes lead to color changes as the fuel is expended. Hockaday describes having dissolved salts in the fuel that come out of solution as the fuel is expended to result in an opaque interior as the fuel is expended. Hockaday describes low permeability single use containers for storing the fuel ampoule until use. This patent does not describe surface tension gradients to segregate liquid, or index of refraction matching of insoluble materials to make transparent. This patent does not describe a background reflector or light transmission through the ampoule. This patent does not describe fluorescing, scintillating, phosphorescent, or quantum dot dyes or means of exciting the dye such as chemi-luminescent or electrical light sources to excite or transmit through the ampoule. This patent does not describe retro-reflectors, insoluble powders or porous inserts. This patent does not describe Bragg reflectors or devices that achieve constructive optical interference. This patent does not describe re-closable storage containers. This patent does not describe using loops of molecular permeable membranes Hockaday U.S. Pat. No. 7,708,553 "Membrane Catalytic Heater" describes using silicone tubes filled with fuel and wicking liners to diffuse fuel to the catalytic heater. This patent does not describe adding powders or dyes to the fuel.

Hockaday U.S. Pat. No. 7,988,984 "Insect Repellent and Attractant and Auto-Thermostatic Membrane Vapor Control Delivery System" this patent describes insect repellent ampoules with membranes permeable to scents, cotton fibers, cloth reinforcing and wicking on the inside of the fuel ampoules, diatomaceous earth, jelling materials, fumed silica, described to maintain liquid contact with the membrane. Hydrating salts, silicone capillary tubes are described but it does not describe surface treatments within the ampoule or surface energy gradients within the ampoule or re-sealable connectors. Dyes added to the scent liquid are not described. A window to the scent ampoules is described but a reflector or light absorber after the ampoule is not described. Problems: The hydrating salts change dimensions growing larger and do not strongly interfere with light when scent oil is removed. The fumed silica and diatomaceous earth still interfere with light transmission and diffuse light, so they are not transparent when wetted. The index of refraction of quartz is 1.46 while the index of refraction of DEET is 1.52 and higher so the miss match allows interfaces still to reflect light when wetted. Cotton fibers index of refraction is 1.56-1.59 and still reflects light when wetted with DEET.

Hockaday U.S. Pat. No. 6,326,097 "Micro-Fuel Cell Devices" Describes looking at the fuel level to assess the quantity of fuel left and fuel tanks with porous filler that goes from clear to opaque when empty. This patent does not describe a molecular permeable membrane as part of the fuel tank or vaporization system.

Chinese Characters Name, Chinese Patent CN 204015230U describes a mosquito repellent delivering high heal shoe with a reservoir, has a sponge evaporation surface and describes micro porous membranes. It uses a floating ring inside the reservoir to indicate the fill level of repellent fluid. It also uses transparent windows to see into the repellent liquid.

McInnes WO 2005118007A1 "Volatile Composition Impregnated in a Porous Carrier and Comprising a Dye as "End-of-Life" Indicator". The product of the present invention can provide a visual indication of this end-of-life point because, after the product has been in use, the dissolved dye precipitates from the porous substrate, such that the original color of the substrate becomes visible. This may give the used product an uneven appearance, for example, with small particles of dye can result in a color change that indicates the end-of-life point of the product. The substrate may be formed of any suitable material. For example, the substrate may be formed of plaster, silica and/or a ceramic material. Preferably, the substrate comprises a synthetic polymer, such as a polyolefin. Suitable polyolefins include polypropylene, high density polyethylene (HDPE), linear low density polyethylene (LLDPE) or low density polyethylene (LDPE). Suitable substrates include Accurel MP from Membrane GmbH. The substrate may be any color. Preferably, however, the substrate is a color that is readily distinguishable from the color of the tube may be a molded tube. The tube has a maximum length of 1 to 3 cm. The outside diameter of the tube may be 1 to 5 mm thick, preferably, 1 to 3 mm thick, more preferably, 1 to 2 mm thick. In a particular embodiment, the liquid composition, for example an air-freshening, deodorizing, pesticidal or insect repellent composition (preferably, the dye dissolved therein) is evenly distributed throughout the substrate." McInnes does not describe matching the index of refraction to make the substrate transparent or if it is transparent at all. He uses the effect of a dye precipitating from the substrate to indicate the end of life color change. McInnes does not describe a molecular permeable membrane reservoir: "Claim 2. A product according to claim 1 wherein the substrate has a mean pore size of from 5 to 20 µm."

Kolbas U.S. Pat. No. 6,718,689B1 insecticide packet membrane allows biting insects to penetrate and suck poison. Kolbas also describes a membrane envelope includes a tube having opposed sealable ends. Kolbas does not use surface tension gradients, index of refraction changes, dyes, or insoluble powders.

Olsen US 20090313883A describes a tubular membrane with dye, calico red, soluble blue II or rhodamine B dyes for a mosquito blood feeder. The mosquitos sting through the membrane to feed. The dyes are used to dye the mosquitos. Olsen describes dusting a powder or dye on the outside of the membrane reservoir to detect insect penetration of the membrane and activity. Also mentioned is texturing on the exterior the membrane for attractiveness to bed bugs. A filling tube is mentioned to fill but it is not as the membrane reservoir. Olsen does not describe a dye or powder inside the reservoir.

Schumacher U.S. Pat. No. 7,917,018 "Wearable Chemical Dispenser" SC Johnson An oval viewing window. Fabric impregnated with metofluthrin a solid. They describe a variety of dye chemicals that can be used as color indicators of concentration in a material and their gaseous departure by virtue of their diffusion out of a material and the resulting color change. As an example Fat Blue B01 is described as used as a chemical color dye that simultaneously diffuses out of polyethylene to act as a parallel expenditure indicator. This patent indicates by simultaneous parallel diffusion the amount scent material and does not directly interact with scent liquids material.

Hayakawa US Patent application, Publication No. US 2002/0016250 A1, "Method for Photocatalytically Rendering a Surface of a Substrate Super Hydrophilic, a Substrate With a Super Hydrophilic Photocatalytic Surface, and Method of Making Thereof". This patent describes photocatalytic surfaces that are self-cleaning when surfaces are subjected to rainfall. This patent mentions fogging of eyeglass lenses and the purpose of the wetting film as an antifogging agent. They found the coating thickness of the order of several nanometers is sufficient to render the surface super hydrophobic. This patent describes using the coating to spread water over heat exchanger surfaces to prevent water condensate from blocking fluid flow heat transfer. This patent does not mention hydrophilic gradients, anti-bacterial, or electrostatic properties.

Minoguchi U.S. Pat. No. 8,048,053B2 Example of a patent utilizing a surface energy gradient: Claim 1. A catamenial tampon having an outer surface, the tampon comprising: a compressed absorbent member having an insertion end, a withdrawal end, a longitudinal axis, and a body disposed between the insertion end and the withdrawal end, the compressed absorbent member having an exterior surface; an auxiliary patch partially covering the exterior surface of the compressed absorbent member; and an overwrap substantially covering the exterior surface; wherein the overwrap at least partially covers the auxiliary patch, and wherein the auxiliary patch comprises a carrier layer and is more hydrophilic than the overwrap to create a surface energy gradient capable of facilitating fluid movement from the overwrap to the absorbent core. Minoguchi does not describe using molecular permeable membranes.

Locko U.S. Pat. No. 4,889,285 Describes diffusion through silicone rubber for diffusion scent delivery and saturation effects the different molecules reach the surface at the same rate and effectively the membrane acts like a very thin membrane. Locko describes using silicone tubing and end caps and delivering fragrance vapor delivery devices. Locko describes using foil packages to contain device until use. Locko does not describe adding powders, dye, or surface tension gradients.

Literature Reference

Momen—Survey of micro/nano filler use to improve silicone rubber for outdoor insulators 1
Rev. Adv. Mater. Sci. 27(2011) 1-13, G. Momen and M. Farzaneh.

SUMMARY OF INVENTION

This invention is a system of a fill capacity indicator for a molecularly permeable membrane reservoir that delivers scent fluids by diffusion. The fill capacity indicator utilizes optical effects of materials placed within the membrane reservoir: index refraction changes, geometric surface energy effects, and light material interactions. Materials with pores and powders with features smaller than several microns can strongly scatter light. If a fluid with a similar index of refraction to the materials with the pores wets the porous material the interface reflection are dramatically reduced and scattering is reduced. If the index of refraction between the fluid and the pores or powders is very close the material when wetted becomes transparent. Porous or powdered materials can be made as part of the membrane wall, or an insert into the reservoir and a light reflector or emitter such as dyes or surfaces can be placed inside or outside of the reservoir. When scent oil wets the porous or powder material and has similar index of refraction there are no interface reflections and it becomes transparent to light. By viewing into or through the membrane reservoir the reflector, emitter, or absorber inside or outside of the reservoir can be seen. The reflector, emitter, or absorber inside or outside of the reservoir can be a dark or colored surface or bright colored light, such that it has a high contrast to when the reservoir is full or empty. When dry of scent fluid the porous or powdered material scatters light and appears white. In most product applications an exterior protective shell is needed so a transparent viewing port or aperture is needed to view the membrane reservoir. The product needs to have a means of allowing light to enter and transmit and be reflected from the ampoule to allow the scent level to be assessed. So arrangements of two windows on either side of the ampoule, a window and an absorber or reflector or a window and light source behind adjacent to the ampoule are needed for this invention to enable the user to view scent liquid levels optical effects. Spatially separated different porosities, geometric surface features, or surface energy treatments, including gradients of these, can be placed inside the reservoir such that they can create progressive liquid drying. This leads to viewable fill indicators that are progressive as the liquid is removed and enabling fractional reservoir fill level indicators.

Micro Porous Materials: As an example, polyethylene has an index of refraction of 1.52 and N,N-Diethyl-meta-toluamide (DEET) a mosquito scent liquid has an index of refraction of 1.52. When DEET wets micro porous polyethylene (0.030 Micron pore diameter) it becomes transparent making it easy to view what is behind the micro porous polyethylene. When a microporous reflector, emitter, or absorber inside or outside of the reservoir polyethylene is dry of DEET the micro pores reflect and scatter light and appears to be white to the viewer.

Powders: Insoluble powders can be mixed into the scent liquid that can act as scattering surfaces when the scent fluid is removed. Colored powders can also add color to the scent fluid when they are suspended in the scent fluid. They can selectively absorb light and reflect light and effectively tint the scent mixture. The powders can be selected such that they have an index of refraction that matches the scent liquid. The powders can be selected such that they have a density similar to that of the scent liquid and they can have a surface energy such that will be wetted by the scent liquid and be retained and submerged in the scent liquid. The powders can confine themselves to the liquid, making the liquid visible, if they are hydrophilic and can form a colloidal suspension in that liquid. Fluorescent, phosphorescent, and scintillating powders can be mixed into the scent liquid as they have the property of coloring the scent liquid. Quantum dots, nano scale semiconductor particles could also be used and their characteristic color emissions can be modified by surrounding the quantum dot in the scent liquid.

Dyes: Adding a dye to the clear scent liquid can improve the visibility and contrast between a filled and empty scent liquid reservoir. This is particularly dramatic if the color of the dye contrasts with the color of the membrane reservoir walls and backgrounds or light sources. The dye can confine itself to the liquid if it is a dissolved substance in that liquid. Dyes in the scent liquid can make the light transmission shift to light scattering and reflecting surfaces more dramatic because the dye can be excluded from the scattering surfaces as it dries, intensifying the dark colors to white reflection change. Some of the dyes also interact with the liquid to produce bright characteristic colors, such as fluorescent dyes, thus when dry the dyes may change color or not emit light and the ampoule will appear to be white or transparent.

Liquid Solid Surface Tension Interface Effects: The form of liquid droplets on a surface can be affected by the geometry of the surface and the surface tension energy of the outer surface atoms of a liquid. The contact angle of the liquid solid interface can vary such that the liquid will wet the surface with a low contact angle or bead on the surface with a high contact angle. Surfaces such as silicone rubber membranes can be treated with a titanium dioxide coating and be rendered hydrophilic. This hydrophilic surface helps water and oils to wet the surface. A surface with hydrophilic and hydrophobic surfaces adjacent to each other will preferentially move water and oil toward the hydrophilic surface. A liquid on a surface that is treated with adjacent zones of hydrophilic and hydrophobic zones can segregate fluid to the hydrophilic areas and enable a progressive appearance change that can be used as a gauge of the remaining fluid in the reservoir. Other techniques to modify the surface tension energy of the membrane surface are to use oxygen ion milling of the surface of the membrane to yield a hydrophilic surface. Ultraviolet light exposure in the presence of oxygen can render surfaces hydrophobic. Oxygen plasma treatment, flame brushing or corona discharge treatments are similar and render surfaces hydrophilic. Coatings or impregnating the membrane surface with hydrophilic materials can render the surface hydrophilic or hydrophobic. Additives such as photocatalytic titanium dioxide and hydrophilic powders can be added to a silicone monomer mixture and polymerized to render the surface hydrophilic. Additives in silicone rubber such as of mulberry-like CaCO3/SiO2 composite particles can lead to super hydrophobic surfaces (Momen, 2011). Co-extrusions of hydrophilic and hydrophobic polymers and rubbers can be created that have surfaces that are hydrophilic and hydrophobic adjacent to each other to be a surface tension gradient. Coating the silicone rubber membrane surface with photocatalytic materials such as titanium dioxide can lead to a hydrophilic surface. Polytetrafluorethylene can be deposited on the tube ampoules to create hydrophobic surfaces. By patterning hydrophobic and hydrophilic surfaces near each other, close enough that a droplet could span the interface between these patterns, then an effective surface tension gradient that can move liquids is created. Creating patterns and fractional coverages can permit the scent liquid to be self-organizing. This self-organization can create the view of the liquid volume to be progressively gauged. The liquid, as its volume changes on a hydrophobic surface, conglomerates into droplets to minimize the surface area to volume ratio. Patterns such as a single bubble that grows larger when filling the tube or small container can be used as a quantitative gauge of liquid volume in that container. The hydrophobic and hydrophilic surfaces can also be patterned to reveal text as the scent liquid is reducing in volume in an ampoule. Surface tension gradients can be used to organize the segregation of gas and liquid in an emptying reservoir so that a repeatable and clear indication of quantity of liquid remaining can be gauged with liquid migrating to the hydrophilic areas from hydrophobic areas over the size of droplets. The effects of the hydrophobicity or hydrophilicity can be intensified by geometrically creating ridges and hairs. Liquids can dramatically increase their contact per unit volume with these surfaces and thereby become dramatically attracted or repelled to these textured surfaces to decrease surface tension energy. Texturing dielectric and semiconductor surfaces down to the nanometer scale also gives them high light scattering properties when there is a difference in index of refraction between the material and surrounding fluid medium.

Materials of tube and connector can have different hydrophobicities (Surface Tension Energy). Diameters of materials closeness of walls can vary to create effects. Treatments of the tube and connector internal surfaces can create differences in surface tension energy. Dyes can be added to enable the viewing of liquid departing from the reservoir. Reservoirs with barbed fitting seals can be opened and remade. The diffusion tube is permeable to the scent liquid and the reservoir is largely impermeable. The reservoir can keep feeding the tube to maintain liquid contact in tube. Gradient of surface tension in the reservoir can lead to a progressive directional empty-out effect (prefers liquid on one side and gas on the other). Viewing through the reservoir the separation of liquid and void space and relative sizes can be used to gauge the quantity of liquid left in proportion to the expended liquid.

By treating the surface of the membranes to wet with the scent oils maintains surface contact between the oil and the membrane. This leads to steady delivery as the scent oil is used up. Impermeable reservoirs should be non-wetting and preferentially permit scent liquids to leave to the diffusion membrane areas.

Electrostatic Effects: Many of the membrane materials such as silicone rubber form permanent electrets and are attractive to liquids with high dielectric coefficients on their surfaces. This attraction preferentially attracts liquid to these surfaces and maintains liquid contact and thereby maintains a steady delivery as the membrane fluid enclosed by the membrane is being used up. We have observed that silicone electret surfaces will hold thin flattened droplets of liquid DEET on the outer surfaces and attribute some of this tight cling of the droplets to electrostatic electrical fields.

Surfactants and Changes to Surface Tension of the Scent Fluid: To change the surface tension energy between liquids and surfaces, and in particular scent oils, surfactants can coat the outer surface and provide a hydrophilic surface on the outer surface of the oil. This allows the scent oils to wet hydrophilic surfaces. Likewise, hydrophobic surfaces can have a surfactant coating the surface and render it more hydrophilic, such as alcohol ethoxylates. Surfactants such as alcohols, such as methanol, ethanol or isopropanol, that reduce the surface tension energy, can be added to the scent fluid that diffuse more rapidly than scent oils through the reservoir such that as the scent fluid gradually as the scent fluid and alcohol are diffused away the fluid inside the reservoir becomes more hydrophobic. This change in wettability of the fluid can result in the fluid segregating itself from hydrophobic surfaces and progressive expenditure indication. Likewise a surfactant added to the scent liquid such as a soap that becomes more concentrated as the scent liquid is diffused through the reservoir membranes. I this case the scent liquid can become more wetting of hydrophobic surfaces and show a progressive expenditure indication.

Retro-Reflectors and Scattering Surfaces: A retro-reflector is an arrangement of an optical system in which light reflects to 180 degree reversal back to the source of light. This is typically referred to as a corner cube when three corners of a transparent material cube are each 90 degrees to each other with the light reflecting off two of the surface facets in the corner to produce a ray of light traveling back to the source. There are a variety of products made for clothing and highway reflectors that utilize this effect. So if the internal reflectivity of the corner cube is reduced by liquid contact to the material interface then the reflectivity of the corner cube is reduced. Corner cubes utilize internal reflections from the solid gas interface. When these surfaces are wetted with scent oil it changes the refraction difference and the reflectivity goes down and the transmission goes up allowing viewing of the background. When the scent oil liquid contact is removed from the corner cube surface the reflectivity goes up and the light reflects out of the scent ampoule. Dielectric scattering surfaces such as powders utilize the index of refraction interface difference between the material and their surrounding fluids or vacuum to reflect light. So when a scattering material such as polyethylene powder with an index of refraction similar to that of DEET are wetted by the DEET the scattering goes to a negligible level and the mixture would appear as transparent to light and enable the viewing of the background.

Similar to the corner cube optics are spherical retro-reflectors. With spherical beads the gas to solid light ray angles change on the incident light into the curved surface of bead and then do internal reflections inside the sphere. When the interface index of refraction difference changes between liquid contact with spherical retroreflective beads the internal reflecting angles inside the bead changes along with the internal reflectivity and the subsequent retro-reflectivity of the beads.

Constructive Interference: A geometric surface of two or more spaced layers can be created that use constructive interference of light to reflect light of particular wavelengths giving the surface an iridescent reflectivity. If the layers are separated with air gaps and scent liquid can fill these gaps the wavelength of the colors can change. The mathematical expression predicting the examples of these layered materials follow Braggs Law of constructive interference and have air gaps between layers (super lattices) such as peacock feathers. When both of these systems are wetted the wavelength of light in the material changes traveling in that media and the subsequent constructive interference color changes. For normal incidence of light to a super lattice the constructive interference color wavelength will be two times the gap spacing times the index of refraction of light inside the space divided by the order of the reflection (1, 2, 3 . . . ). As an example, an air gap spacing of 225 nm between partially reflective metal reflector layers will produce a constructive interference of light of 450 nm when the Bragg reflector is in air. If the lattice were completely filled with DEET instead of air and the reflective layers are thin (index of refraction of 1.52 and the wavelength will be shortened by 1/1.52) the first order reflection would result in a constructive interference reflection at 684 nm wavelength (a red light). This color change from liquid to dry state can be used to gauge filled or empty in a scent ampoule. If the reflectivity depends on the index of refraction reflections at each interface of the materials in the system, by wetting between the layers the interface reflectivity will go down and subsequent constructive interference reduced. If a grating reflector that depends on interface reflection has an index of refraction at 1.52 then the reflectivity is reduced to zero and no constructive interference would be observed.

Electric light Sources: Electric light sources can be located behind the ampule such that the scent ampoules can be viewed by light transmitted through the ampoule enabling the ampoules to be viewed at night. LED lights can be made small enough and be packaged such that they could be the illumination source behind the scent ampoules. Photovoltaics and batteries could be used as the electrical power source for the electrical lights. Fuel cells that run on emissions from the scent ampoules could power electrical lighting. In several applications, such as nighttime safety marking, the back illumination light source can also serve as the entire wrist band illumination source. The light source emissions can have a wavelength of light that stimulates a characteristic emission from the scent oil, dye, or powder added to the scent oil to make it visible and contrast with the background and the ampoule walls.

These and further and other objects and features of the invention are apparent in the disclosure, which includes the above and ongoing written specification, with the claims and the drawings.

BRIEF DESCRIPTION OF THE DRAWINGS

FIG. 17A Perforated cover cap to be inserted into the slap band cavity.

FIG. 17B Slap band.

DETAILED DESCRIPTION OF PREFERRED EMBODIMENTS

Figure 1:
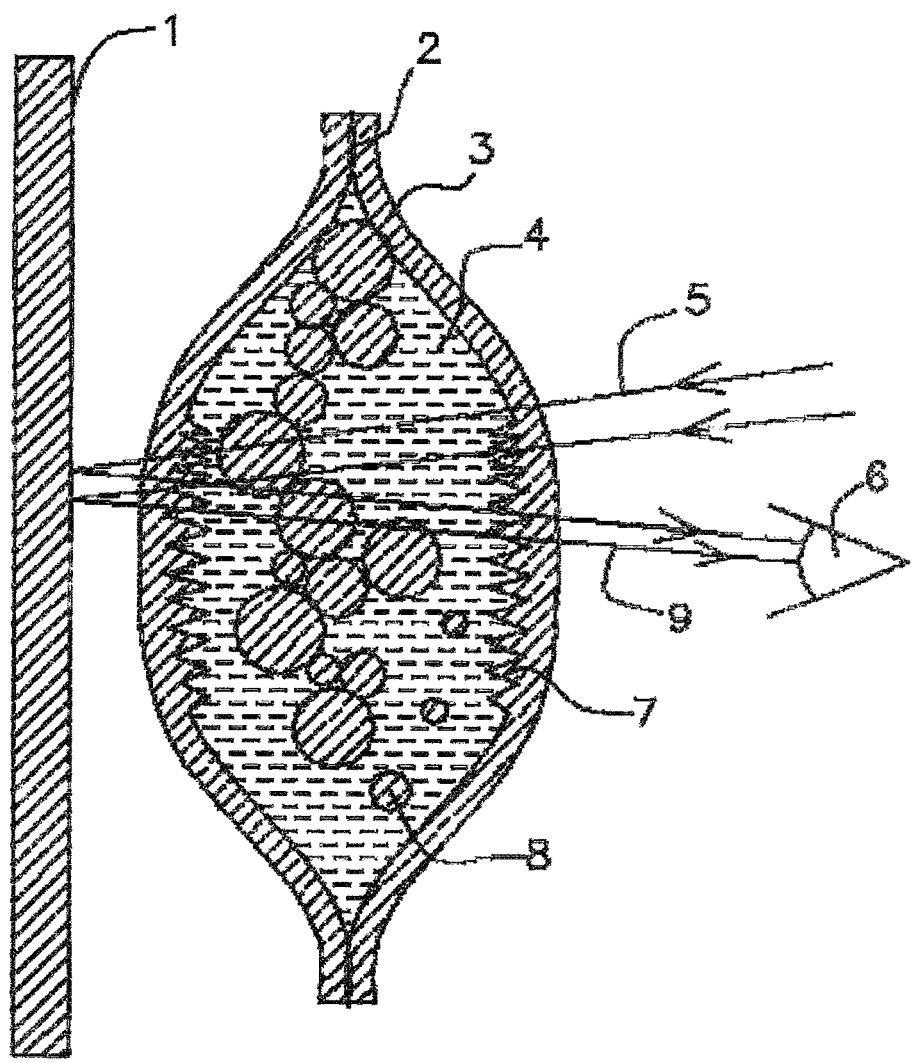
FIG. 1 Cross sectional view of scent liquid filled molecularly permeable membrane ampoule with scattering surfaces inside ampoule.

In FIG. 1 a cross-sectional view of scent liquid filled molecularly permeable membrane ampoule with scattering surfaces inside ampoule is shown. To form this ampoule two layers of a selectively permeable membrane sheets 3 (0.25 mm thick) with inner surface texturing are created with a roughened surface 7 by molding or etched the inner surface of the membrane to a surface roughness scale bellow 0.1 mm features and (Specialty Silicone Products, Inc., Corporate Technology Park, 3 McCrea Hill Road, Ballson Spa, N.Y. 12020). The ampoule can also be formed with a range of molding techniques. The roughened membranes are glued 2 together using silicone sealant (General Electric Silicone I). The membrane can be reinforced by bonding to a porous polyethylene fiber membrane (Tyvek, DuPont) or fiberglass mat. A mosquito repellent mixture of such as 10 micron diameter polyethylene powder 8 (Mipelon™, Mitsui Chemicals America, Inc. 800 Westchester Ave., Suite S 306, Rye Brook, N.Y. 10573) (MPP-635XF polyethylene 4-6 micron diameter spheres, MicroPowders Inc., 580 White Plains, Rd. Tarrytown, N.Y. 10591) suspended in N,N-Diethyl-meta-toluamide (DEET) 4 (Vertelus 2110 High Point Road, Greensboro, N.C. 27403, USA). The DEET 4 has an index of refraction of 1.52 and polyethylene of 1.51 to 1.54. DEET has a specific gravity of 0.996 and the specific gravity of polyethylene is 0.91 0.97 (Low density polyethylene to high density polyethylene). DEET will wet polyethylene so polyethylene powders 8 can form as colloidal mixture. This is a transparent mixture of DEET and polyethylene scattering particles. The silicone rubber ampoule walls 3 depending on the polymer formulation have an index of refraction of 1.4 to 1.465 and with polymer chain group substitutions the index of refraction can go as high as 1.55. The textured walls when wetted with the DEET scent liquid 4 as shown in FIG. 1 can be transparent to incident light 5 when the DEET makes liquid wall contact 7. This scent liquid filled ampoule is placed with holder with a back plane wall 1 and viewed by the user 6. The back plane wall can absorb light or selectively reflect light to give it a color appearance such as black, red, and blue printed on polyester plastic membrane 1, which are colors that contrast well with white when the ampule is emptied of scent liquid. Black or red are attractive colors for mosquitos and can be used to distract mosquitos away from the user's skin. The backplane can also be a fluorescer, scintillator or phosphor that absorbs light and remits in a characteristic color such as anthracene loaded polyester plastic membrane. The colored light 9 or lack of light that is transmitted through the ampoule is observed by the viewer to indicate the ampoule is filled. In operation the scent liquid in the ampoule diffuses through the ampoule walls 3 delivering a steady rate. In operation the DEET diffuses through the membrane walls to provide mosquito repellency for the user and the quantity of DEET gradually declines. As the liquid volume declines the polyethylene particles 8 are brought closer together and deposited into the channels of the roughened surface of the silicone membrane 7.

Alternative powders to be added to the liquid repellent 4 could be spherical retroreflective beads, scintillating particles, quantum dots, phosphor particles, and fluorescing particles 8. Spherical retroreflective glass beads typically have an index of refraction of 1.7 and 1.95. When they are wetted with the scent liquid such as DEET 4 the entrance angles inside the bead changes and the internal reflections are much lower. Thus the retro reflections are dramatically reduced. In this example the ampoule 3 would be transmissive to light when filled with scent liquid and then reflective when the scent liquid is expended.

If scintillating crystals are used as the powder additive 8 they have the property that when wetted with a matching index of refraction liquid the excitation light can efficiently reach the scintillation crystals and the emitted light can efficiently travel out of the scintillating crystals. When they are dry they scatter the excitation light off their surfaces and the light that is captured results in scintillation and a small fraction of the light escapes the scintillating crystal.

Figure 2:
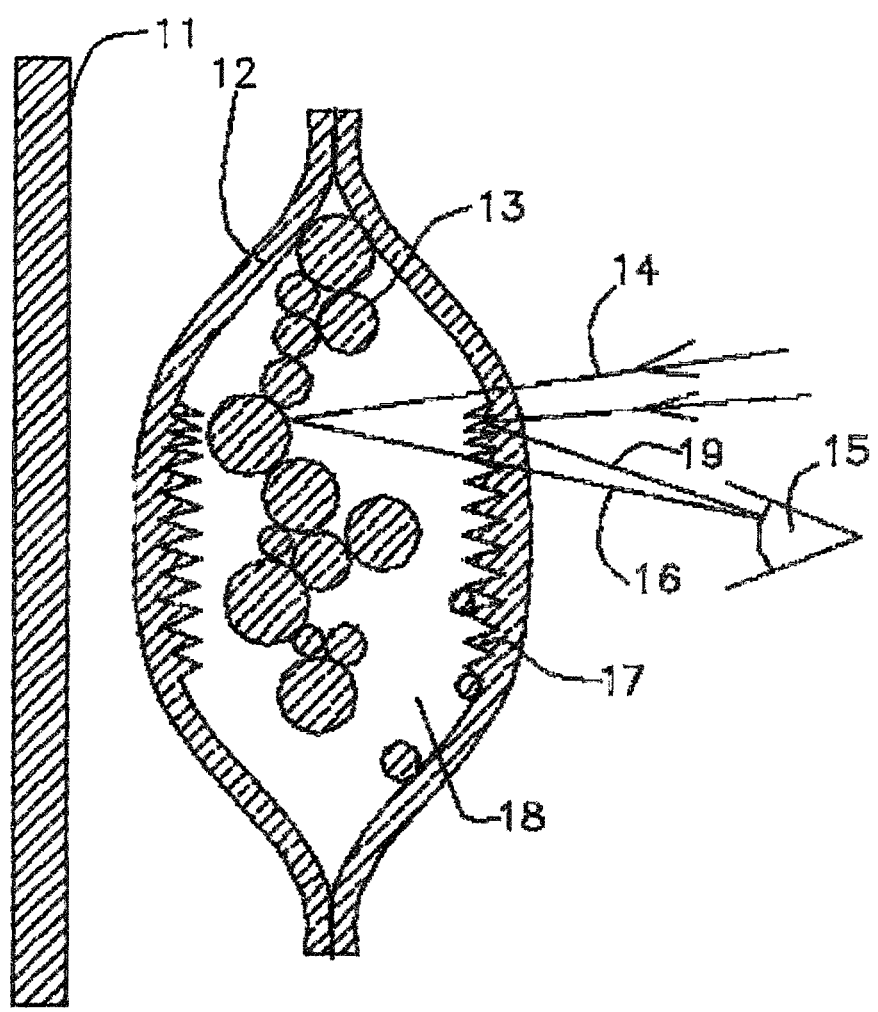
FIG. 2 Cross sectional view of empty molecularly permeable membrane ampoule with interior scattering surfaces.

In FIG. 2 a cross sectional view of empty molecularly permeable membrane ampoule with interior scattering surfaces is shown. When the polyethylene particles 13 and channels 17 of the roughened surfaces are dried of DEET by outgoing diffusion through the molecularly permeable silicone membrane 12 the ampoule is simultaneously filled by diffusion with air 18. Incident light 14 scatters 19,16 off the gas solid membrane interfaces of the membrane 17 and the polyethylene particles 13 scatter white light 19,16. As viewed from exterior looking at the molecularly permeable ampoule 12 when emptied the scent liquid polyethylene powder 13 is white and the background surface 11 is not viewable. When the DEET liquid is expended by diffusing out of the ampoule membrane walls 12 the scattering off the colloidal particles 13 the ampoule appears to be white to the viewer 15. Through the course of the liquid DEET being expended the surfaces 17 are exposed progressively depending on interface surface tension differences such that the light scattered from the ampoule is gradually whitening giving the user a graded expenditure indication. This enables the viewing user 15 to be alerted that the ampoule is near expenditure and they can choose to refill the ampoule or replace the ampoule to continue the use of the ampoule for scent delivery at an effective delivery rate for mosquito repellency.

Figure 3:
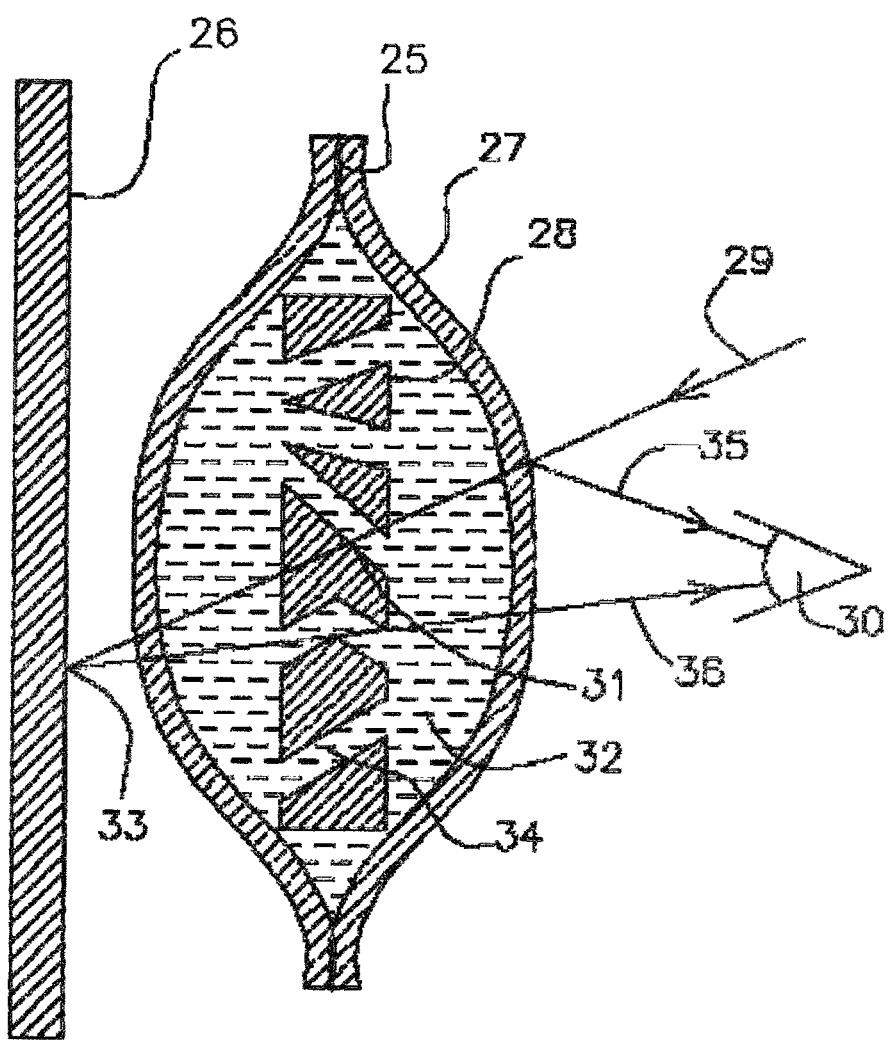
FIG. 3 Cross sectional view of scent liquid filled molecularly permeable membrane ampoule with porous membrane inside.

In FIG. 3 a cross sectional view of scent liquid filled molecularly permeable membrane ampoule is shown with a micro porous high density polyethylene film 25 microns thick, 0.030 micron average pore size, 40% porosity 28, (Made by Mobil Chemical Company, Films Division, 729 Pittsford, Palmyra Rd. Macedon, N.Y. 14502) inside the walls of molecular permeable silicone membrane 27. The molecularly permeable membrane 27 could also be a 0.05 mm thick low density polyethylene membrane heat sealed around the perimeter 25. The polyethylene 27, 28 has an index of refraction of 1.52 and scent liquid 32 has an index of refraction of 1.52. When the scent liquid 32 is infused into the pores 34 of the porous polyethylene 28 it is transparent to light 29. This allows light to transmit through the molecularly permeable membranes 31, 28,27 and the porous membrane to background 33, 26. Small amounts of reflected light 35 would occur on the outer surface of the molecularly permeable membrane 27 and be observed by user 30. The background 26 could be a dark light absorbing surface 33 or a reflector combined with the scent liquid 32 being color dyed such that the observer sees a characteristic color of light 36 or lack of light coming back through the ampoule 27, 32, 28. A dye could be added to the scent liquid 32 to reflect light or emitted 36 from the scent liquid giving it a color viewed by the observer 30. The porous film 28 could act as a sponge with the pores 34 impregnated with scent oil 32 such as citronella oil or lemon of eucalyptus and cooled to be a solid. This frozen scent membrane 28 is placed within a tube of 0.05 mm thick polyethylene 27 and heat impulse sealed 25 with compression to form a sealed ampoule.

Figure 4:
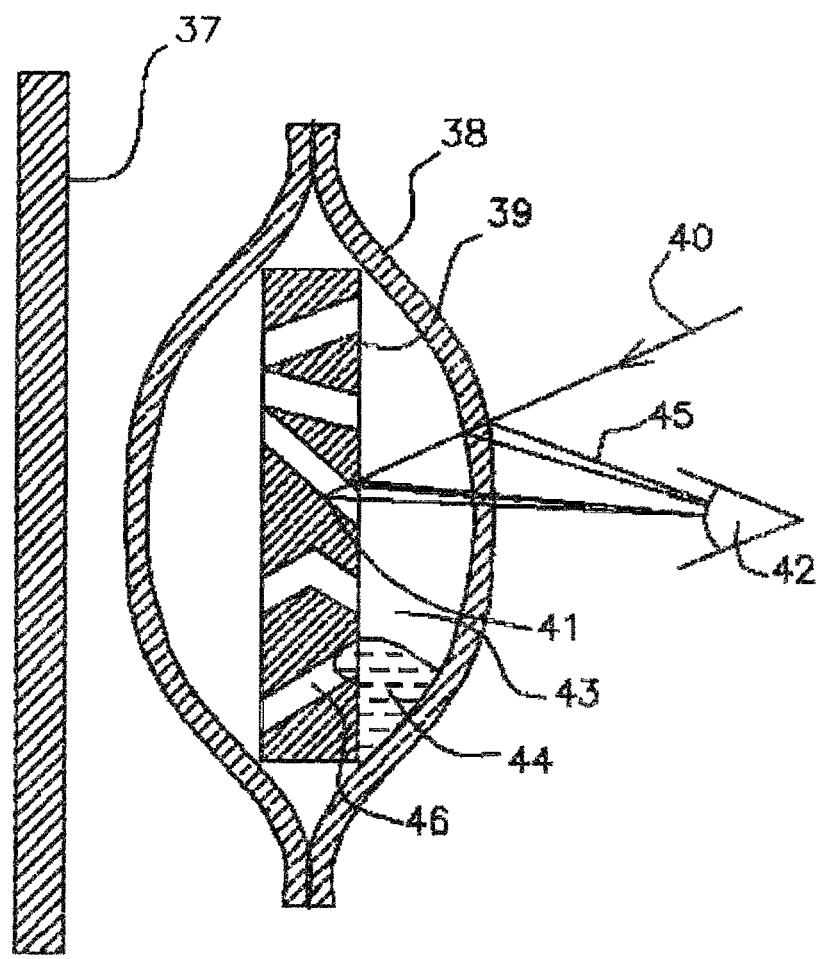
FIG. 4 Cross sectional view of near scent liquid empty molecularly permeable membrane ampoule with porous membrane inside.

In FIG. 4 a cross sectional view of an empty molecularly permeable membrane ampoule with a porous membrane is shown. The scent liquid has diffused out of the ampoule with air 43 diffusing into the ampoule through the molecularly permeable membrane 38 ampoule and the porous polyethylene membrane 39. The porous polyethylene membrane 39 scatters incident light off multiple gas to solid interfaces in the porous membrane 41. To the observer 42 the porous polyethylene 39 appears to be white and there also are reflections of light 45 off the molecularly permeable membrane 38 air solid interfaces. The porous polyethylene membrane blocks light transmission to and from the background 37. The remaining scent liquid and dye 44 conglomerate into droplets, preferentially forming outside of the hydrophobic pores 46 of the porous polyethylene 39. To minimize surface tension energy the droplets of scent liquid 44 between the hydrophobic porous membrane 39 and the polyethylene molecular permeable membrane 38 conglomerate into droplets. They reduce their area and present little viewable area to incident light 40 such that the porous membrane appears to be white with scattered light to the observer 42.

Figure 5:
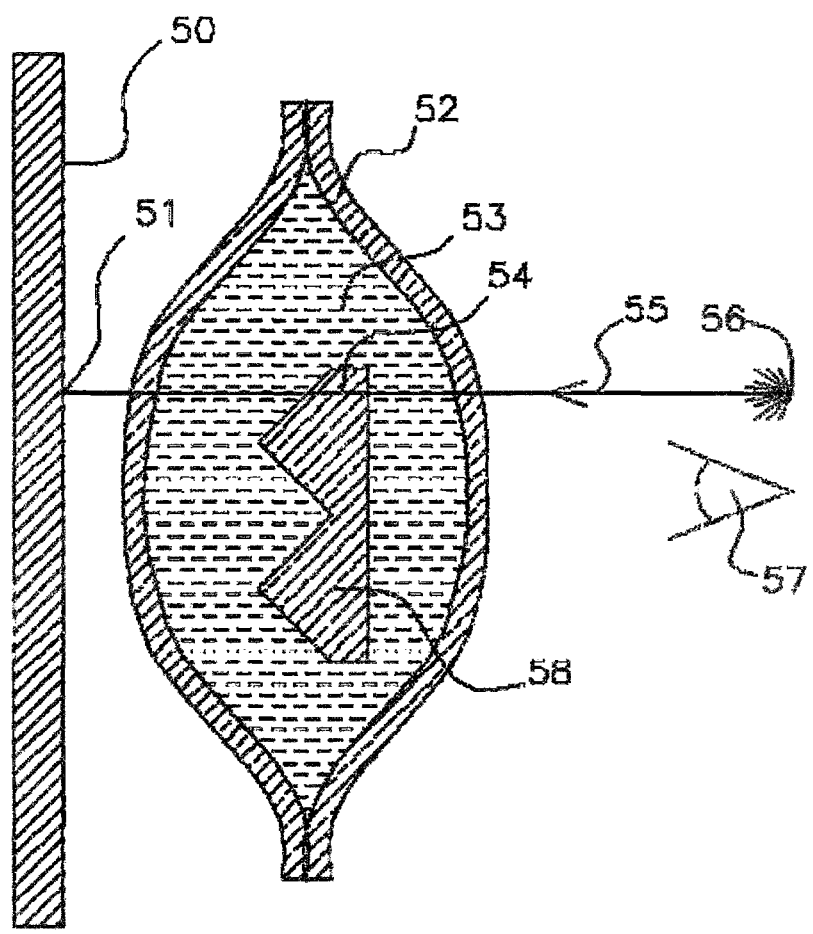
FIG. 5 Cross sectional view of scent liquid filled molecularly permeable membrane ampoule with retro reflectors.

In FIG. 5 a cross sectional view of scent liquid filled molecularly permeable membrane ampoule with retro reflectors is shown. As an example corners of a cube of a transparent dielectric material such as glass with three smooth flat sides each at 90 degrees to the other is a retro-reflector facets 58. Incident light 54 from the inside of the glass that strikes one surface will partially reflect as an internal reflection of the solid air interface and second surface such that it will reflect back toward the incident light ray. Arrays of retro-reflector facets with internal reflections can be created. As an example these arrays can be made out of glass with an index of refraction of 1.52. Corner cube arrays are commonly used as highway reflectors. The corner cube array is placed inside the silicone rubber ampoule molecularly permeable membranes 52 and filled with DEET insect repellent 53 with an index of refraction of 1.52. Due to the index of refraction matching between the glass 58 and the DEET 53 there will be no reflectivity at the interfaces and the corner cube reflectors will not reflect incident light 56, 55 back and transmit through the reflector array 58 and to a background 50. The background can absorb the light or allow colored light to be reflected 51 and transmitted back through the corner cube array 58 to the observer 57. Dyes such as fluorscene can the added to the insect repellent mixture to add characteristic colors to transmitted and reflected light.

Figure 6:
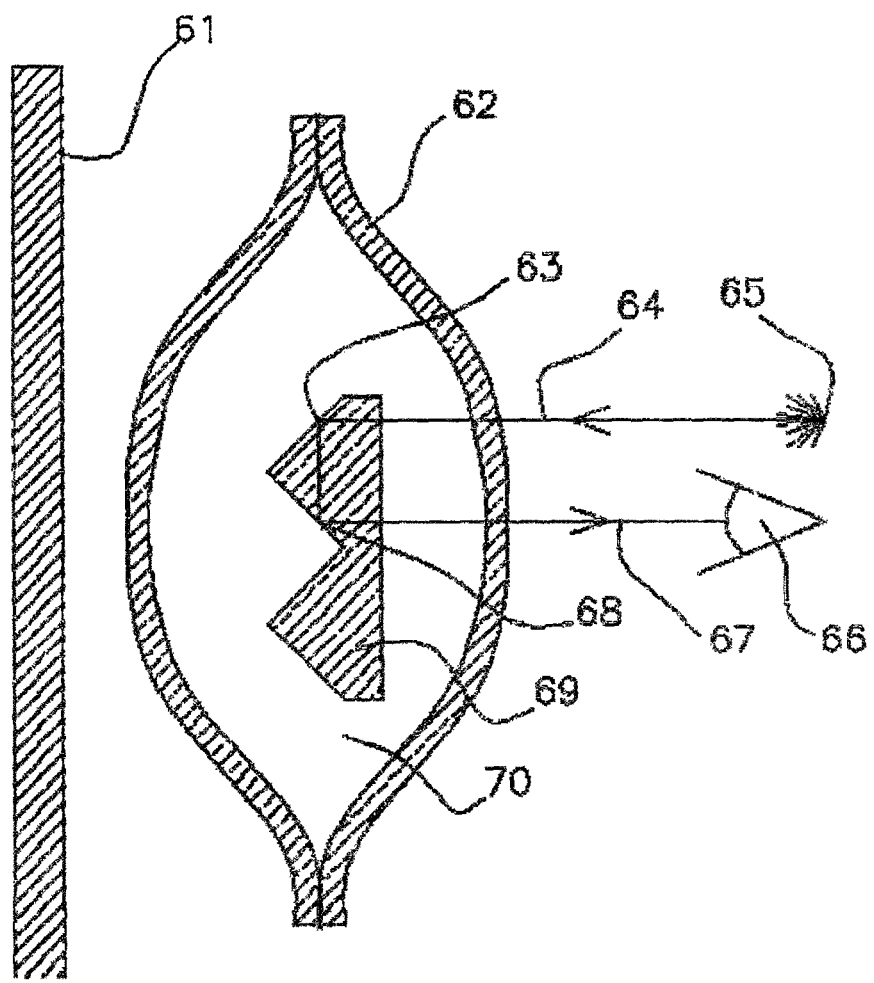
FIG. 6 Cross sectional view of empty molecularly permeable membrane ampoule with interior retro reflector.

In FIG. 6 a cross sectional view of empty molecularly permeable membrane ampoule with corner cube array reflector is shown. Scent liquid DEET has been removed by diffusion through the molecularly permeable membrane while air 70 has diffused into the ampoule though the molecularly permeable membrane 62. The corner cube 69 surfaces are dried and the incident light undergoes internal reflections off the 90 degree surfaces 63 with the glass air interfaces of the glass corner cube array. Incident light 64 from a light source 65 is reflected 67, 68 and observed 66 and will give the observer a view of bright reflection out of the scent ampoule contrasting with the back ground 61 light absorption when the ampoule was filled with scent liquid. If an array of corner cube reflectors 69 are spaced in a regular array with spacing of similar to the wavelength of light this array could enable constructive interference of the light and colorful reflections of light when the observer is viewing the array at angles from normal incidence. These type constructive interference reflections are observed in butterfly wings and could be used to enable a positive means of confirming that the scent ampoule is empty.

Figure 7:
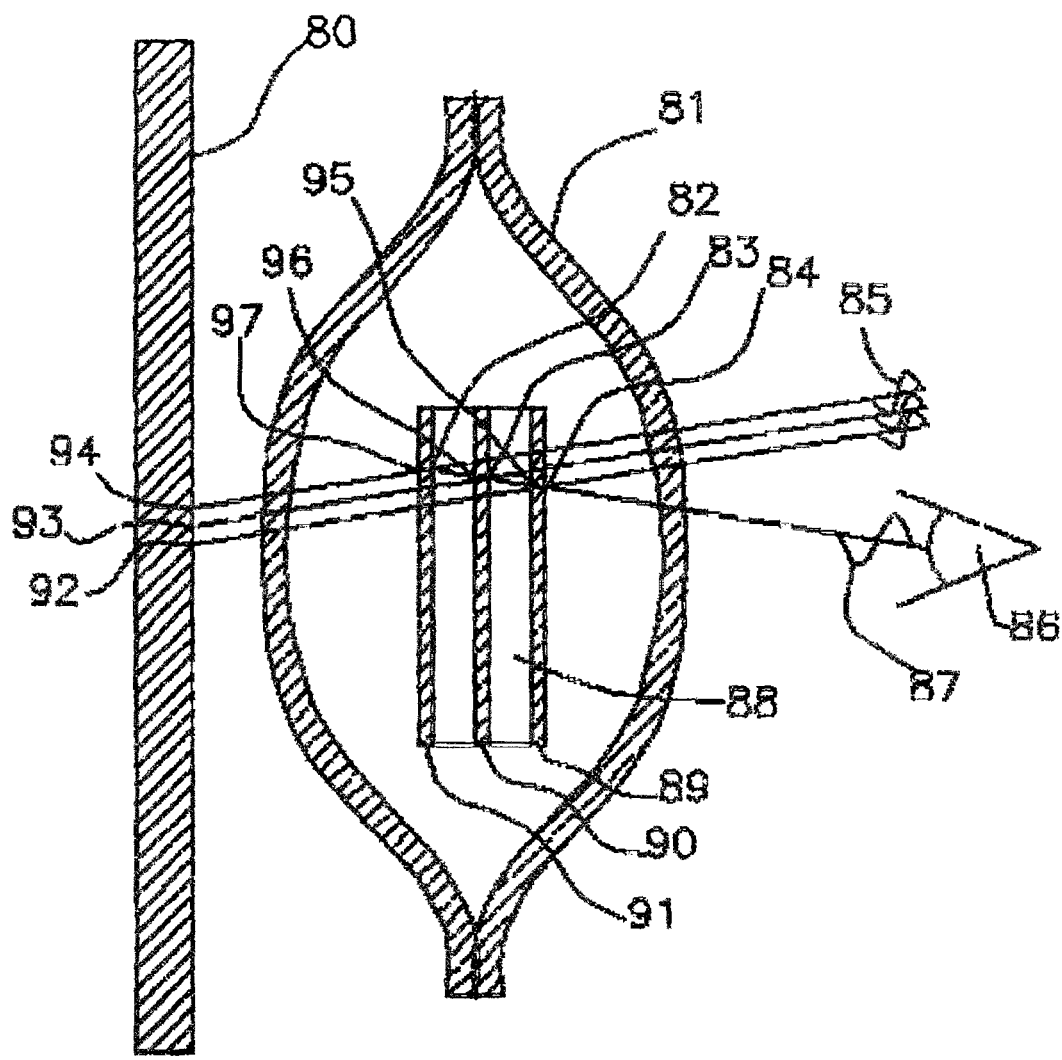
FIG. 7 Cross sectional view of scent liquid filled molecularly permeable membrane ampoule with super lattice Bragg reflectors.

In FIG. 7 a cross sectional view of an empty molecularly permeable membrane ampoule with super lattice Bragg reflectors or layer reflective materials are shown. Dielectric layers of transparent materials 89, 90, 91 with hollow gaps between the layers 88 are formed that can obtain Bragg Reflections that are placed within a molecularly permeable membrane 81 ampoule. The layers of Bragg reflectors, in first order, a surface reflection 89 is paired with an internal reflection 95 a quarter wavelength thickness away. Then an internal reflection 95 is paired across an air gap and next external reflection 83 a quarter wavelength away. This sequence is repeated into the Bragg reflector to enable all reflections 84, 83, 82, 95, 96, 97 off the dielectric air 88 interfaces to produce a construction interference of incident light 85. This is the equivalent to a dichroic filter with an air gap layer 88 and produces a bright constructive interference reflection of light 87 observed by the user 86 when the ampoule is filled with air 88.

Alternatively, if thin semi reflective and transmissive layers of metal were deposited on each layer 89, 90, 91 each layer would be a half wavelength of light achieve first order constructive interference. Incident would constructively interfere off the interfaces and be observed as constructive interference reflected light 87 by the observer 86. Transmitted light will travel on to the background 80 and be absorbed 94, 93, 92.

Figure 8:
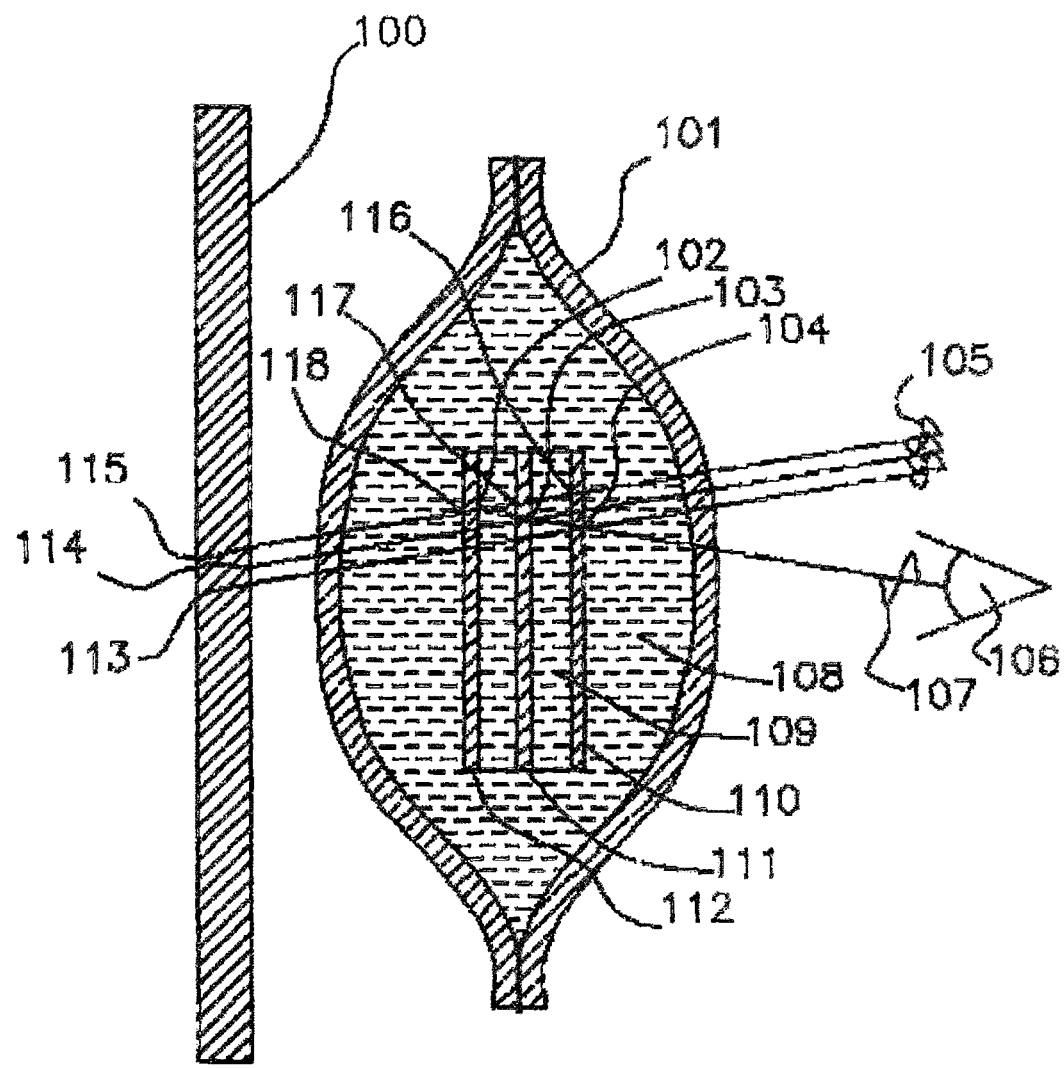
FIG. 8 Cross sectional view of empty molecularly permeable membrane ampoule with super lattice Bragg reflectors.

In FIG. 8 a cross sectional view of scent liquid filled molecularly permeable membrane ampoule with super lattice Bragg reflectors is shown. When the scent liquid DEET fills the ampoule 108 and fills the air gaps 109 in the super lattice material 110, 111, 112 the wavelength of light will be shortened. This will change the constructive interference between layers and in the case of metal layer reflectors 104, 103, 102 will cause the constructive interference of the light 107 to be shifted to longer wavelengths of light (red shifted).

In the case where the reflectivity of each layer interface 116, 117, 118 depends on index of refraction differences this will shift the light reflections across the gaps and destroy the constructive interference. If index of refraction between the solid 110, 111, 112 and infused liquid 108 in the Bragg reflector are matched there will be no reflections 102, 103, 104, 116, 117, 118 and also no constructive interference 107 and the light will be absorbed 113, 114, 115 by the backplane 100. For the observer 106 when the ampoule is filled with scent liquid 108 the ampoule will appear to be dark and as the scent liquid is diffused out through the membrane 101 and leaves the super lattice 110, 111, 112 the ampoule will produce colorful constructive interference Bragg reflections 107 of a light source 105 as viewed by the observer 106.

Gratings and holograms that depend on dielectric interfacial reflections to reflect and scatter light can also be used as an indicator of wet or dry conditions in an ampoule. With gratings there will be no shift due to change in wavelength of light incident on the grating because the angles incident will also change. The dominating effect will be the reflectivity changing with liquid contact to the dielectric medium interfaces.

Figure 9:
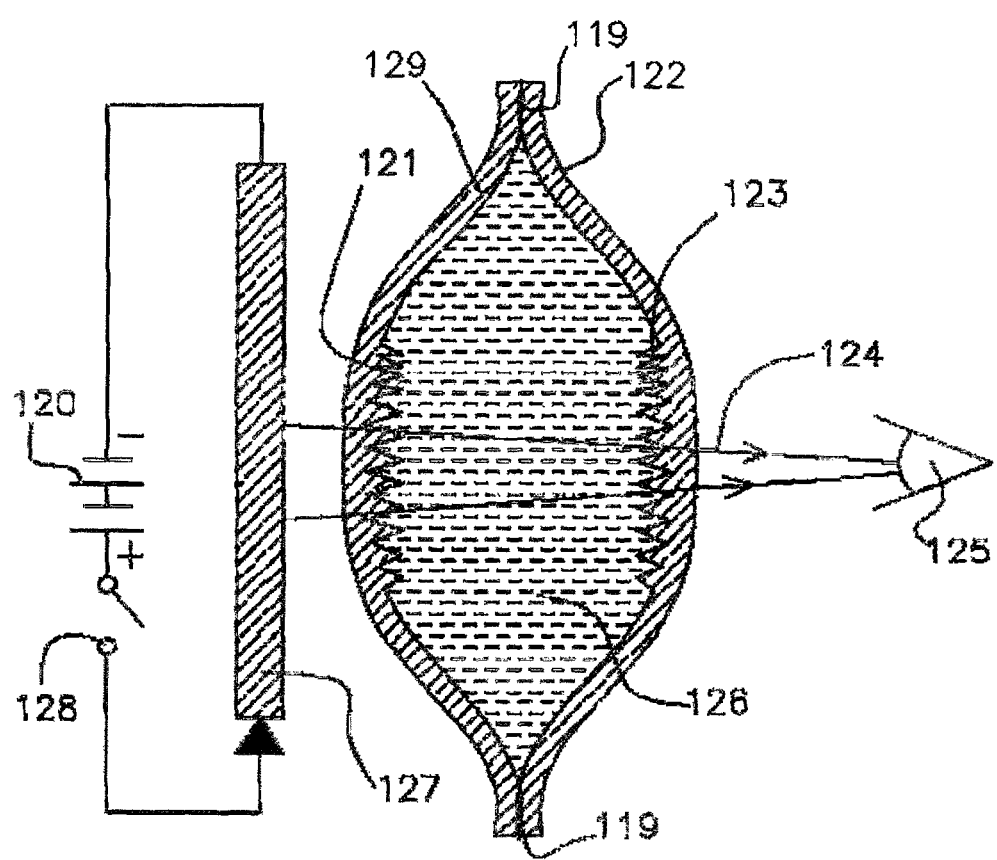
FIG. 9 Cross sectional view of scent liquid filled molecularly permeable membrane ampoule with hydrophobic textured membrane surfaces.

In FIG. 9 a cross-sectional view of scent liquid filled molecularly permeable membrane ampoule with hydrophobic textured membrane surfaces is shown. Two 0.20 mm thick silicone rubber ampoules 122, 129 are formed by molding, or extrusion that have textured features 121, 123 on the membranes with groove or protuberance features smaller than 0.1 mm with aspect ratios higher than 1. The silicone rubber sheets are glued together, 119 to form a hollow cavity and DEET or DEET and dye 126 is injected with a needle syringe through the glue joint area 119 to completely fill the ampoule 129 122. Incident light 124 on the ampoule will travel through the interfaces at the silicone (1.4 to 1.55 index of refraction) to the DEET (1.52 index of refraction) with low reflections off the interfaces 121, 123. Ambient light will travel through the ampoule 129, 122 to be absorbed or reflected off the dyed scent fluid 126 or background 127. The viewer can see reflected or transmitted light from the background 127 and emitted or reflected light from the scent fluid 126. The background 127 could be a light source such as an electrically stimulated light source such as organic light emitting diode, light emitting diode, incandescent lamp, light pipe from a light source, or cell phone screen 127. The background 127 could be light sources of fluorescer, phosphor, scintillator, or sunlight scattering through a diffuser. In some applications the repellent or attractant ampoule and protective housing are placed on a light source 127 to attract mosquitos or disorient and confuse mosquitos. The light source 127 could be a steady or flashing light source to act as a night safety marker. The light source 127 could be a short wavelength light source that could stimulate the characteristic fluorescent light emissions from the dyed scent liquid 126 enabling a rapid visual assessment of the liquid quantity by the viewer 125 observing light transmitted from the source 126 or stimulated emissions from the scent liquid and dye 126. The electrical power for the stimulated light source 127 could be batteries 120, or photovoltaic cells, fuel cells, thermoelectric, piezoelectric, or kinetic electromagnetic sources of electrical power. Electronics, shown as switch 128, could be used to control the light source 127.

Figure 10:
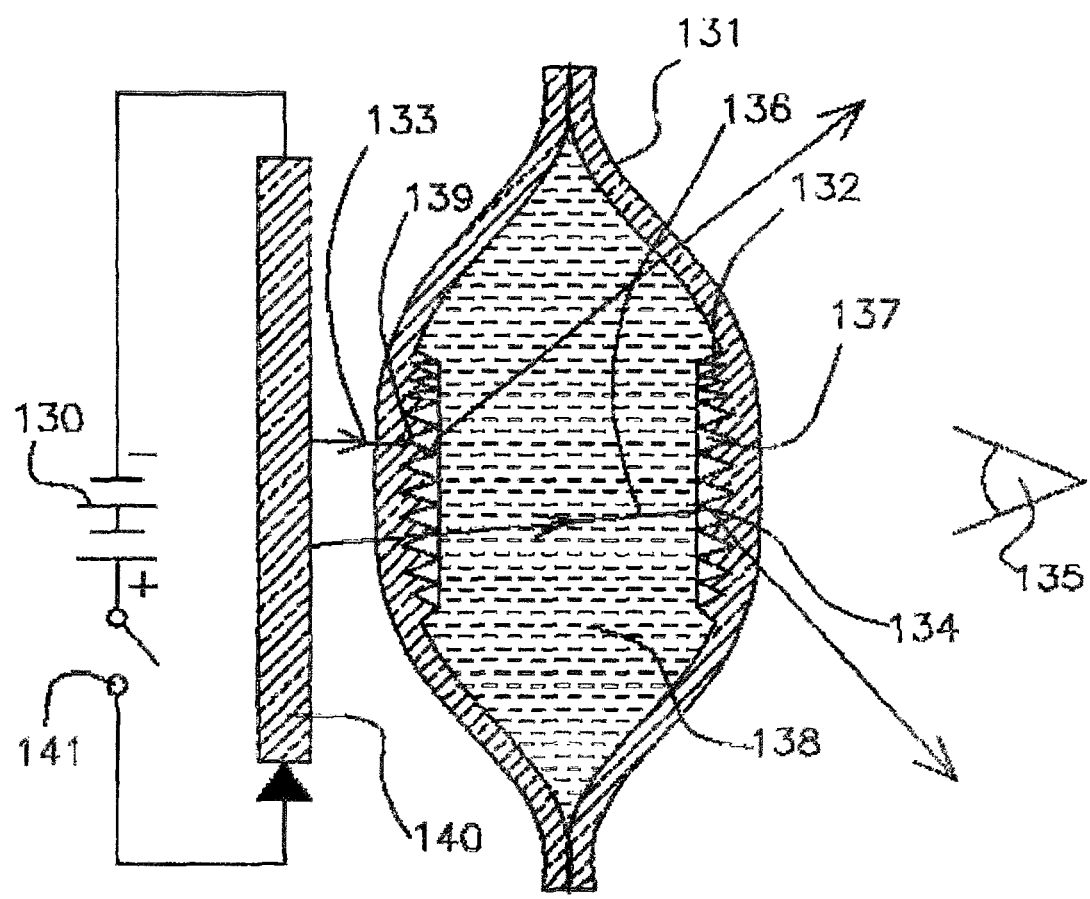
FIG. 10 Cross sectional view of empty molecularly permeable membrane ampoule with hydrophobic textured membrane surfaces.

In FIG. 10 a cross sectional view of partially empty molecularly permeable membrane ampoule with hydrophobic textured membrane surfaces is shown. As the scent liquid 138 is removed by diffusion through the molecularly permeable membranes 131, air 132 will diffuse into the ampoule 131. The air gas bubbles 137 will form in the grooves 132. Air diffuses in and scent fluid diffuses out through the molecularly permeable membranes 131, and by a surface tension gradient effect of tapering the hydrophobic channels 132, the liquid can reduce surface tension energy by leaving the grooves 132. This leads to the grooved area preferentially drying out and forming gas/dielectric interfaces in the grooves 134, 139 that will reflect and scatter light 133, 136. The observer 135 will see more reflectivity from the grooved surfaces and the ampoule could gradually become whiter as more of the hydrophobic textured surfaces 134, 139 are exposed. The grooving and texturing of the membrane surface 131 could be done by laser etching the surface. Micro texturing the surface to preferentially dry and be visible can lead to two dimensional patterns such as symbols and text being visible as the scent liquid is depleted and an indicator of the fill level. The viewer 135 will progressively view more scattered and less directly transmitted light from the background electrical light source 140, 141, 130 as the scent liquid diffuses through the molecular permeable membrane 131 and the textured surfaces 132, 134,139 of the silicone membranes 131 dry out.

Figure 11:
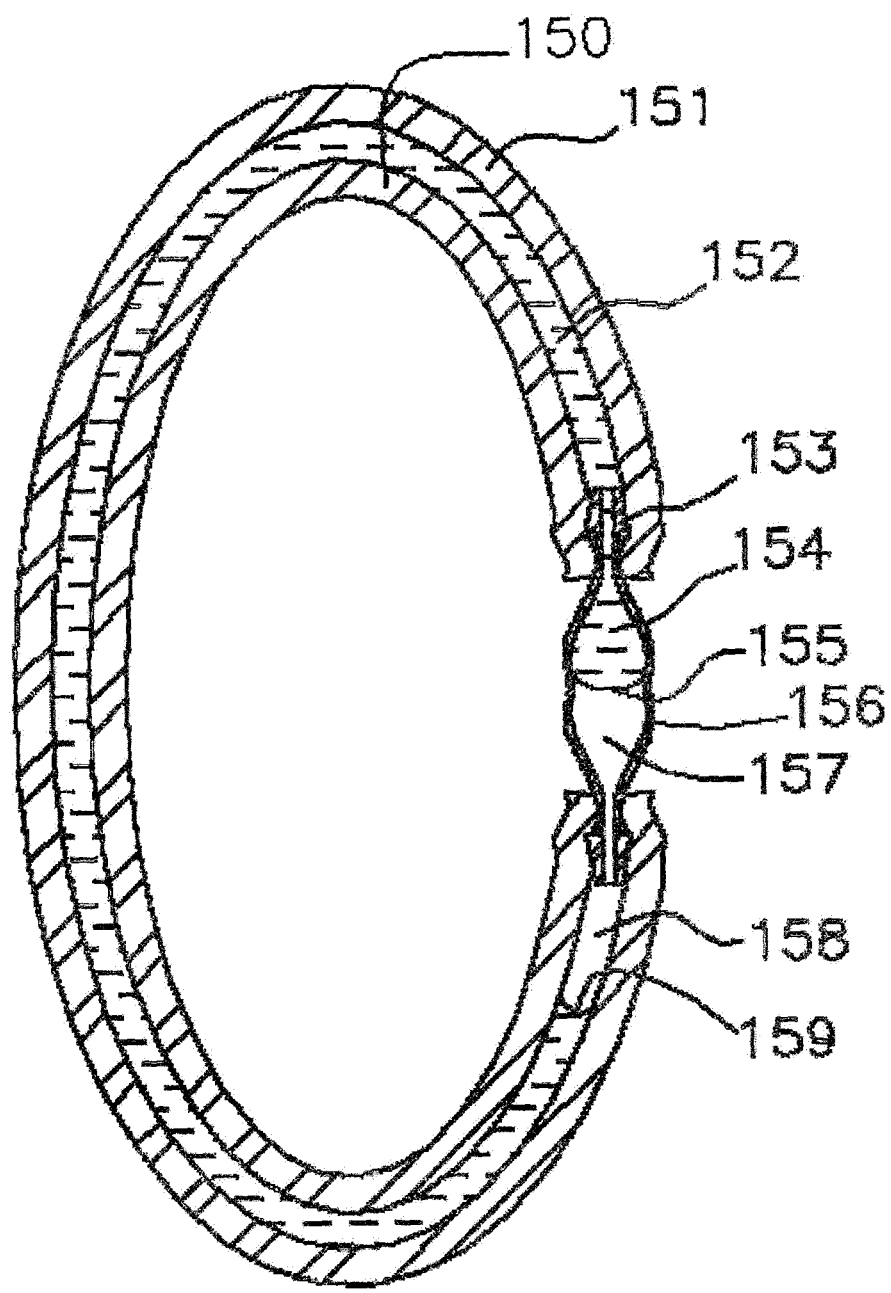
FIG. 11 Cross sectional view of scent liquid filled molecularly permeable membrane tubular ampoule with connector.

In FIG. 11 a cross sectional view of scent liquid filled molecularly permeable membrane tubular ampoule with a barbed connector is shown. A silicone tube 150, 151 with 2 mm outside diameter and 15 mm inside diameter and 1.11 meters long (Hangzhou, Xineng Electric Technology Co, Ltd, Hengxi Industrial Estate, Jincheng Street, Lin'an, Hangzhou, China) is filled with 1 ml of DEET (N,N-Diethyl-meta-toluamide) (Vertelus, 2110 High Point Road, Greensboro, N.C. 27403, USA), 0.8 ml of Oil of Lemon Eucalyptus p-Menthane-3,8-diol, (Citrefine International Limited, Moorefield Road, Yeadon, LEEDS, LS197BN, UK) and powdered sodium sulfate $Na_2SO_4$ 154. A dye such as fluorescein can be added to the scent liquid mixture 154 at a concentration of 6 ppm to make the liquid more visible and give it a fluorescent green tint. Another possible dye is Rekhaoil®Bronze Dye (Narad Marketing Corporation, PO Box1817 Clifton, N.J. 07015). The polypropylene barbed 153 connector 156 (Eldon James Corporation, 10325 East 47$^{th}$ Avenue, Denver, Colo., 80238) can be corona discharge surface treated to have one end 153 be hydrophilic and the other end 157 remain hydrophobic. This will insure that as the ampoule depletes the scent liquid the liquid exits out one side of the connector driven by the hydrophilic/hydrophobic gradient. The silicone tube 150, 151 can be treated with a titanium dioxide coating that is solution deposited with methanol and dried and heat cured (TPXsol Kon Corporation, 91-115 Miyano Yamauchi cho, Kishima-gun, Saga prefecture, Japan). The titanium dioxide particle deposit enables the silicone tube interior to wet 159 and insure liquid contact with the scent fluid 152. The contact angle 159 of the liquid is shown to be low in the silicone tube and high in the hydrophobic end of the connector 157. The polypropylene connector is a non-diffusion reservoir so it could be used to increase the volume capacity of the ampoule without increasing the membrane 150,151 diffusion surface area. In operation, the scent liquid diffuses through the silicone rubber membrane 150, 151. As the scent liquid is depleted air also diffuses into the ampoule creating bubbles in the tube 158. The bubbles zones are transparent and the remaining liquid retains the dye and is a characteristic color of the dye. By viewing the ampoule with liquid 152, 154, and gas portions 158, 157 the remaining capacity can be gauged by the fraction of the tube occupied by the dyed scent liquid 152,155.

Figure 12:
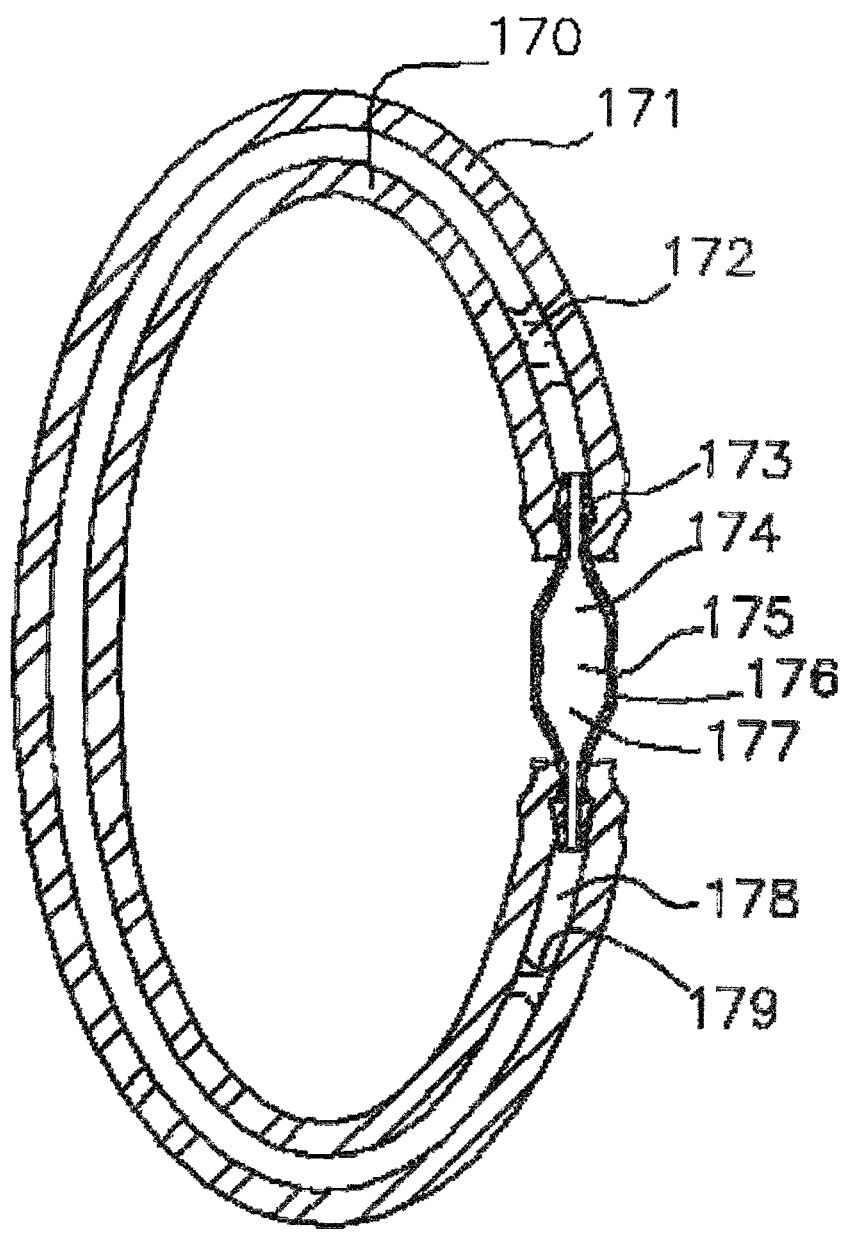
FIG. 12 Cross sectional view of empty molecularly permeable membrane tubular ampoule with connector.

In FIG. 12 a cross sectional view of empty molecularly permeable membrane tubular ampoule with connector is shown. As the scent liquid diffuses out through the tubular ampoule membrane walls 170, 171 the scent liquid 172, 179 is depleted and coalesces due to surface tension into droplets in the tube with dyes following being retained in the liquid. Simultaneously air 178 diffuses in to a fill the tubular ampoule 171. The barbed connector 173 by the action of the hydrophobic 176. 177 to hydrophilic 174 surface gradient empties of DEET and fills with air 175 from the silicon tube 171, 175. Within the ampoule 170, 171 the scent liquid can evaporate and condense on the walls of the ampoule in thin films or micro droplets. Fluorescein dye will come out of solution and deposit as small nonvisible red deposits so there is no green fluorescent emission or dying of the silicone tube 170, 171. These condensate films are transparent and not easily viewable. The larger droplets 172, 179 that hold the dye are easily viewable with the colors contrasting with the surroundings. As a further means of distracting mosquitos, the dye colors are chosen to be red or pink to be attractive to mosquitos hunting blood. The remaining dyed liquid droplets 172, 179 appear as colored segments in the tube. The fractional volume of remaining scent fluid can be estimated by looking at the filled length and dividing by the total length of the tube. This gives the user a quantitative assessment of the remaining liquid.

Figure 13A:
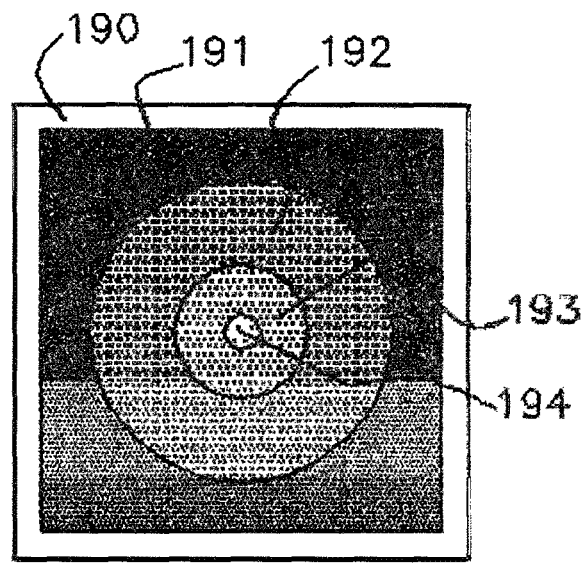
FIG. 13A Hydrophilic and hydrophobic patterned liquid segregation in molecular permeable membrane ampoule.

In FIG. 13A a hydrophilic and hydrophobic patterned liquid segregation in molecular permeable membrane ampoule is shown. A silicone rubber membrane wall 191, 192, 193,194 is etched, molded or laser cut to form a texturing with pores or grooves in a pattern of lowest density in pores 194 in the center of the pattern and a progressively higher density 193, 192 toward the perimeter 191, of the sheet of membrane 190. The pores of the membrane 191, 192, 193, 194 can be treated to be hydrophilic to attract the scent liquid.

Figure 13B:
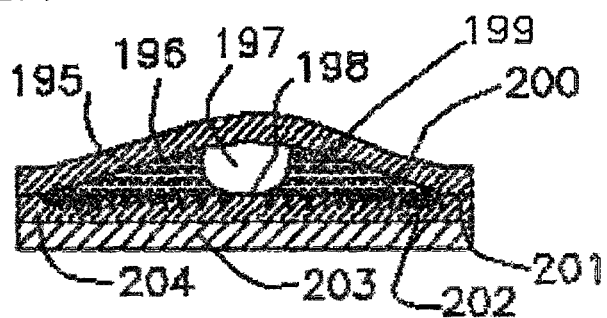
FIG. 13B Cross sectional view through the hydrophobic and hydrophobic gradient patterned ampoule filled with scent liquid.

In FIG. 13B a cross sectional view through the hydrophobic and hydrophobic gradient patterned ampoule filled with scent liquid is shown. An upper molecular permeable membrane of silicone rubber 195 untreated to remain hydrophobic and a backing membrane 203 are stacked on either side of patterned membrane 190, 191, 192, 193, 194 shown in FIG. 13A. The membrane stack is laminated on the perimeter 190 to a surface and a backing film 201, 204. The backing membrane 203 of silicone rubber or metal foil of aluminum could be chosen to be a contrasting color or white to contrast with the color of the dyed scent liquid 196, 199. A scent liquid mixture 196, 199 is injected into the ampoule 195, 203. The scent liquid diffuses through the molecular membrane 195 and simultaneously air 197 diffuses through the membrane 195 into the gas bubble 197. The in diffused air forms bubbles 196 that coalesce into the largest volumes and most hydrophobically bounded upper silicone membrane surfaces 195,198. In this example the upper silicone rubber membrane 195 is hydrophobic and the contact angle of scent liquid is a high angle, while the lower pore bearing membrane is hydrophilic and the scent liquid has a low contact angle with the surface 198. The shape of the ampoule cavity can also be effective in providing large cavity that tapers out to thin cavity that helps to amplify the hydrophilic region 200, 202 to hydrophobic region 198 bubble formation centering in the ampoule. For an observer looking down on the ampoule they would observe the bubble in the center 197 allowing light to transmit to the backing sheet 203 and see then the characteristic color of the backing sheet 203 reflecting back and scattering off the textured surface 198. While the areas covered by the dyed scent liquid 196, 199 would be absorbing light and have its characteristic color emission or reflection as it blocks or reduces the light transmitting through the liquid wetted hydrophilic patterns 200, 202 to the backing film 203. The pattern of the central dot and perimeter can give the observer a visual gauge of fractional area of the ampoule's remaining liquid compared to the total volume.

Figure 13C:
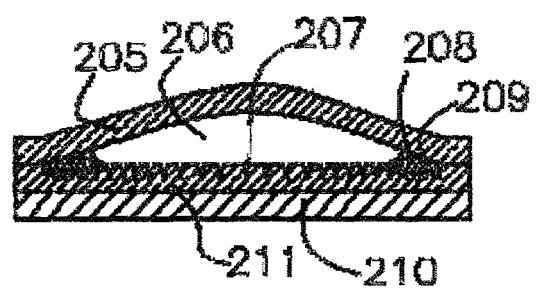
FIG. 13C Cross sectional view through the hydrophobic and hydrophobic gradient patterned ampoule filled with remaining scent liquid in hydrophilic corners.

In FIG. 13C a cross sectional view through the hydrophobic and hydrophobic gradient patterned ampoule filled with remaining scent liquid in hydrophilic corners is shown. In this illustration the majority of scent liquid has diffused through the membranes 205 and small droplets 208 remain in the corners 209 on the patterned membrane 211. The majority of the volume of the ampoule is filled with air 206 that has in-diffused through the silicone membrane 205. In operation the backing membrane 210 has prevented unwanted diffusion from the bottom layer of the ampoule facing a product container wall. This is particularly relevant when this ampoule is used in human wearable products where diffusion of repellents toward the human skin is not desirable. The remaining scent liquid 208 in the ampoule has coalesced to where high hydrophilic pore density is the highest 209 and attracting the scent liquid and dye mixture away from the hydrophobic regions 207 where the pore density is lowest. For the viewer of the ampoule, the majority of the ampoule has an air bubble in it and the background is viewable. A small perimeter scent liquid with dye 208, 209 is visible. This ampoule is nearly fully expended.

Figure 14A:
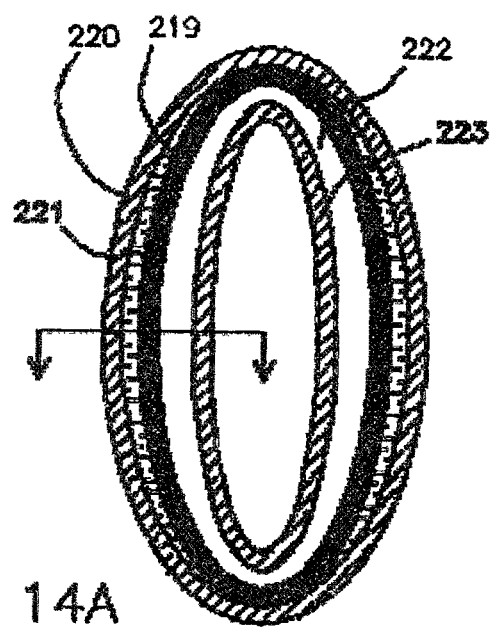
FIG. 14A Cross sectional lengthwise view of molecularly permeable tubular ampoule with hydrophilic segregation of liquid to capillary channels.
Figure 14B:
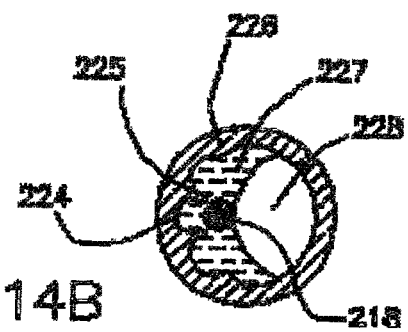
FIG. 14B Cross sectional view perpendicular to molecularly permeable tube ampoule with hydrophilic capillary channel separation half full of scent liquid.

In FIG. 14A a cross sectional lengthwise view of molecularly permeable tubular ampoule with hydrophilic segregation of liquid to capillary channels is shown. This ampoule 220, 223 is formed as a tube with an asymmetric cross section with small channels on one side 224 as shown in FIG. 14B. The small channels and large channel tube 223, 220 can be extrusion molded from silicone rubber. Powders that render the surface of the silicone rubber channeled or textured and/or hydrophilic can be added to the silicone monomer when extruding to produce the asymmetric hydrophilic/hydrophobic tube. The tube filled with scent liquid 221 that is dyed wets the walls of the tube 220. Surfactants could be added to the scent liquid to enable the scent liquid to wet silicone rubber 220. The scent liquid 221, 227 is preferentially attracted by the higher surface energy of the smaller channels 224,225, 226. Alternatively, the small channels could be rendered to be hydrophilic with a surface treatment while the large channels 222, 228 retain the hydrophobicity of the silicone rubber 220, 223. So as the scent liquid is expended by diffusing out of the ampoule 220 the scent liquid is attracted and coalesces on to the small channels or protuberances 224,225, 226. A similar means of forming a one sided capillary attraction on the side of the tube is to incorporate a much smaller porous wicking thread 219, such as polyester white thread, or an extrusion inside of a larger hydrophobic tube 220. As the scent liquid is expended the liquid will coalesce to the smaller wicking thread. If the scent liquid is dyed the thread 219 will hold the liquid and will color contrast with air filled tube. The wicking or flow in the capillary channels 224, 225 also helps to evenly distribute the remaining scent liquid along the length of the tubular ampoule to maintain diffusion delivery rates though the membranes 220, 223.

In FIG. 14B a cross sectional view perpendicular to molecularly permeable tube ampoule with hydrophilic capillary channel separation half full of scent liquid is shown. As the scent liquid 227 diffuses through the molecularly permeable silicone rubber membrane tube 226 air diffuses into the tube and forms an asymmetric air bubble in the tube 228. The dyed liquid 227 coalesces to the small channeled 225, 224 side of the tube 226. As viewed from the outside, the ampoule changes from a uniform color to a two color system with dyed scent liquid on one side 227 with the background being the second color. A wicking thread 218 can be added that is immersed in the scent liquid.

Figure 14C:
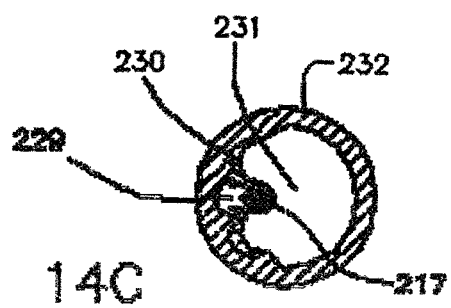
FIG. 14C Cross sectional view perpendicular to the molecularly permeable tube ampoule with hydrophilic capillary channel separation of remaining scent liquid.

In FIG. 14C a cross sectional view perpendicular to the molecularly permeable tube ampoule with hydrophilic capillary channel separation of remaining scent liquid is shown. The scent liquid 230 is almost completely expended and the scent liquid has coalesced to the small capillary tubes 230, 229. For the viewer, the ampoule would appear to be nearly completely expended with a small fraction of the scent liquid dye 229, 230 being visible on one side of the ampoule tube 232. The remainder of the ampoule tube will be filled with air 231, and being transparent, the background can be viewed. The viewer can look at any segment of the tube and observe the same appearance so that only a small segment of the scent ampoule needs to be viewed to diagnose the fill level in the ampoule. A wicking thread 217 can be added that holds part of the remaining scent liquid and dye. When the ampoule liquid 229 is expended, a thin tinted thread 217 will be visible from the outside depending on the color of the dye when it is dried on the polyester thread 217.

Figure 15A:
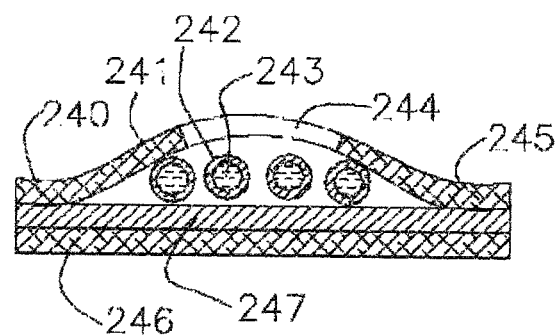
FIG. 15A Cross sectional view of porous tubular band with molecular permeable tubular membranes and viewing port.

In FIG. 15A a cross sectional view of tubular band or packet with molecular permeable tubular membranes and viewing port is shown. For this example a tubular ampoule 242 is shown placed within a stack of porous non-woven polyethylene membrane 241, impermeable polyester membrane 247, and non-woven polyethylene membrane 246. The polyester membrane 247, has been treated to enable it to heat seal to the polyethylene membranes 241, 246 and it serves the purpose of blocking un-needed scent diffusion toward the band user. This polyester membrane 247 can also be printed with a color and pattern to enable a contrasting background to the scent ampoules 242, 243. The top porous non-woven polyethylene membrane 241 has one or more viewing apertures 244 cut to allow viewing of the ampoule's 242 scent liquid 243 level. These viewing apertures 244 could also incorporate window membranes to protect the ampoules and still allow viewing. The stack assembly can be compression heat sealed 240, 245 along the perimeter or the ampoules inserted after the compression heat sealing.

Figure 15B:
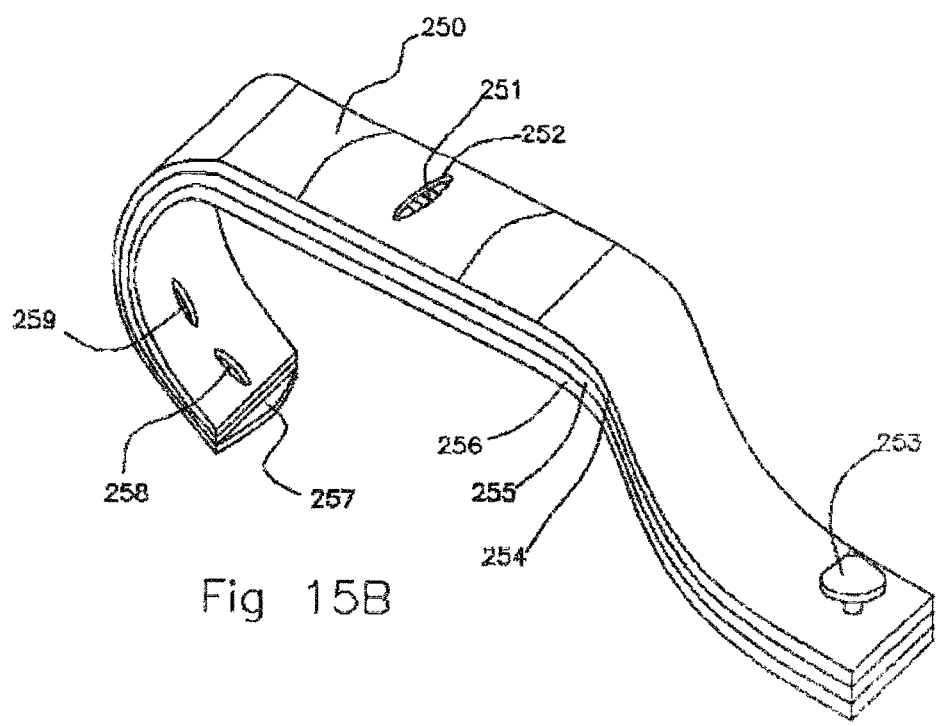
FIG. 15B Porous tubular band with molecular permeable tubular membranes with viewing port and button fasten system.

In FIG. 15B a porous tubular band with molecular permeable tubular membranes with viewing port and button fasten system is shown. The lamination of the non-woven polyethylene 254, 256 and the polyester 255 forms a hollow band 250. In this example one end of the band is open ended 257 to allow the insertion of the scent ampoules 251 and button holes 258, 259. At the other end of the band 250 is a rivet button 253 that allows the tubular band 250 to be strapped around a wrist or ankle. In the middle area of the band 250 a viewing aperture 252 allows the ampoules to be directly viewed. In this example it is an elliptical hole. The viewing port 252 can be stylized to be part of printed patterns on the band 250 and, in particular, can form an eye pattern that is attractive to mosquitos. The non-woven polyethylene band 250 can be printed with colorful patterns for the user's preferences. The non-woven polyethylene 254, 258 was chosen to be water proof and breathable to enable diffusion and air flow from the ampoules 251 and from the user. The layer 256 that is in contact with the human could be a wicking fabric or felt that permits soft contact and air flow. In operation the band is strapped on the human wrist, ankle or hat using the choice of button holes 258, 259 to find an appropriate fit. The human can check the fluid level by looking through the viewing port 252

Figure 16:
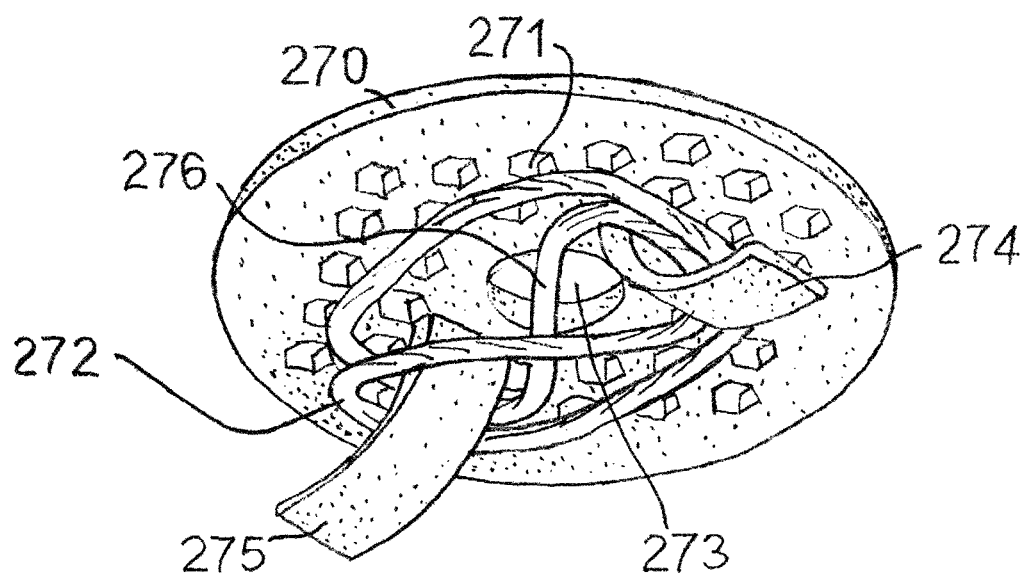
FIG. 16 Perforated reel cover cap with wound tubular ampoule.

In FIG. 16 a perforated reel cover cap and wound tubular ampoule is shown. The cover cap 270 is injection molded from polypropylene plastic with reel legs 274, 275 (Proto Labs Inc. 5540 Pioneer Creek Drive, Maple Plain, Minn. 55359). The tubular ampoules 276 are wound around the legs 274, 275 of the reel cap 270. The filled tube windings 276 include winding the tube across the center to permit viewing of the tube ampoules through the center aperture 273. The vent holes 271 distributed throughout the cover cap provide the emission venting from the tubular ampoule.

In FIG. 17A a perforated cover cap to be inserted into the slap band cavity is shown. The viewing aperture 281 is shown facing out and the tubular ampule 282 will go inside the slap band cavity 291 held by the legs 283. The rim 280 of the perforated cover cap fits inside the rim 290 of the rubber slap band cavity 291. The legs 283 of the cover cap 280 fit within the corners of the slap band cavity and form an protected ventilation cavity 291 with vent holes 284 inside the slap band 292.

In FIG. 17B a slap band is shown. A silicone rubber slap band is formed with silicone rubber injection molding about a bi-stable tempered steel band 292 (J&F Silicone Rubber Products Factory, Qiuhu Road, Qiuchang Town, Huiyang District, Huizhou City, China). The slap band has a cavity chamber 291 and an overhanging sleeve 290 to hold rigid objects in the cavity 291.

Figure 17C:
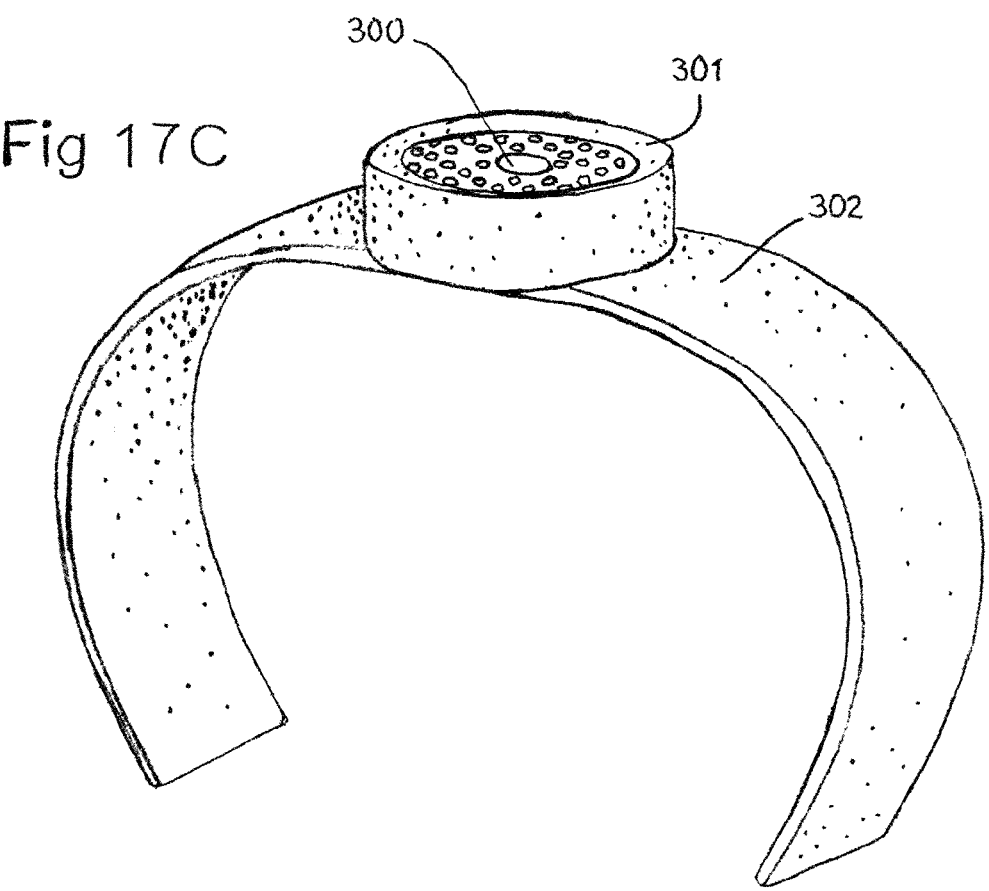
FIG. 17C Slap band with tubular ampoule and reel cap.

In FIG. 17C a slap band with tubular ampoule and reel cap is shown. The assembled reel with tubular scent ampoule is inside the cavity and held by the rubber sleeve of the silicone rubber slap band 302. In operation the slap band 302 will lay flat (first stable form) until bent around a wrist or ankle and go to the second stable form of a curled sheet to create a loop on the user's ankle or wrist. When the user observes that the scent liquid fractional quantity is low by viewing through the center aperture 300 the user can refill the ampoule pulling the reel assembly 300 out of the slap band by pulling back the rubber sleeve 301. Refilling ampoules can be done by injecting liquid either by needle syringe injection through thickened areas of the silicone rubber ampoules or by opening the tube ampoule at the connector tube joint and refilling with a syringe.

Figure 17D:
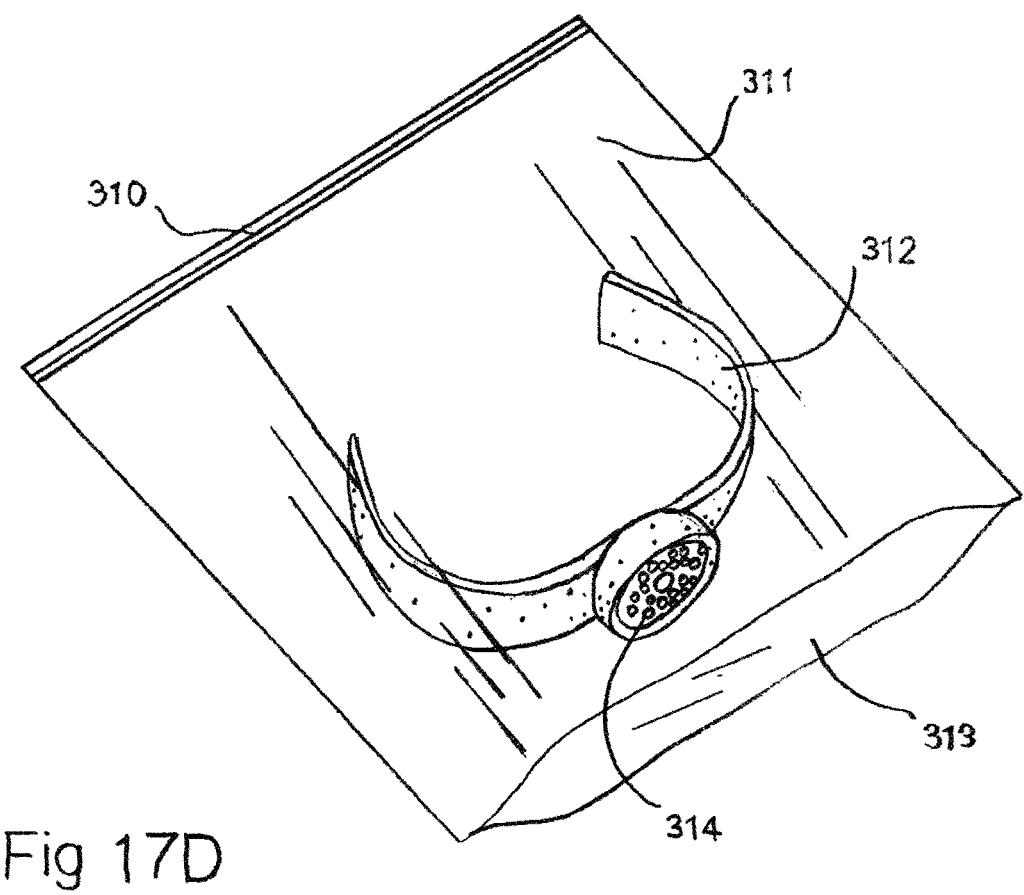
FIG. 17D Slap band with a tubular scent ampoule shown placed in a resealing bag.

In FIG. 17D a slap band with a tubular scent ampoule is shown placed in a resealing bag. The assembled slap band with the scent ampoule or ampoules are placed in an air tight container, heat sealed polyester or heat sealed polyethylene/metal foil bag to be held until use. The assembled band can be replaced back in an air tight container or zip-closure polyester bag to be stowed with low scent fluid loss until reuse.

Dyes can be added to the scent mixture such that when the scent liquid is present the liquid specifically absorbs light to make the ampoule have a color or is dark. When the scent liquid is removed, the light scattering prevents the light traveling into the residues of the dye and the ampoule appears to be white or colorless.

While the invention has been described with reference to specific embodiments, modifications and variations of the invention may be constructed without departing from the scope of the invention described in the claims.

LIST OF COMPONENTS IN FIGURES

FIG. 1 Cross sectional view of scent liquid filled molecularly permeable membrane ampoule with scattering surfaces inside ampoule.
1. Back plane light absorber, emitter, and reflector
2. Seal ampoule area
3. Molecular diffusion membrane
4. Scent liquid
5. Incident light
6. Optical observer
7. Roughened high surface area membrane wall
8. Light scattering particles, porous membrane, or fibers
9. Reflected or emitted light transmitted through ampoule FIG. 2 Cross sectional view of empty molecularly permeable membrane ampoule with interior scattering surfaces
11. Back plane light absorber
12. Molecular diffusion membrane
13. Light scattering particle or fiber
14. Incident light rays
15. Light observer
16. Light scattered from particles or fibers
17. Light scattered off roughened surfaces
18. Air void in ampoule
19. Light scattering from roughened surface to observer FIG. 3 Cross sectional view of scent liquid filled molecularly permeable membrane ampoule with ruled transmission grating
25. Heat seal
26. Back plane absorber
27. Molecular permeable membrane
28. Porous membrane
29. Incident light
30. Optical observer
31. Light rays incident and transmitting through porous membrane
33. Light incident on back absorber
34. Scent liquid filled in pore
35. Surface reflections of light
36. Back transmitted light FIG. 4 Cross sectional view of empty molecularly permeable membrane ampoule with ruled transmission grating
37. Back plane absorber
38. Molecular permeable membrane
39. Porous membrane
40. Incident light
41. Reflection of incident light
42. Optical observer
43. Air in ampoule
44. Remaining scent liquid and dye
45. Reflected and scattered light rays
46. Hydrophobic pore FIG. 5 Cross sectional view of scent liquid filled molecularly permeable membrane ampoule with retro reflector
50. Back plane light absorber
51. Light incident on light absorber
52. Molecular permeable membrane
53. Liquid scent
54. Light passing through retro reflector facets
55. Light rays
56. Light source
57. Observer
58. Retro light reflector facets with matching index of refraction to scent fluid FIG. 6 Cross sectional view of empty molecularly permeable membrane ampoule with interior retro reflector
61. Back plane light absorber
62. Molecular permeable membrane
63. Internal reflection
64. Incident light ray
65. Light source
66. Observer
67. Reflected light ray
68. Second internal reflection
69. Retro reflector sheet
70. Air in ampoule FIG. 7 Cross sectional view of scent liquid filled molecularly permeable membrane ampoule with super lattice Bragg reflectors
80. Back plane light absorber
81. Molecular permeable membrane
82. Reflection off layer
83. Reflection off layer
84. Reflection off layer
85. Incident light waves
86. Optical observer
87. Constructive interference of reflected light
88. Scent liquid within super-lattice
89. Reflective layer 90. Reflective layer
91. Reflective layer
92. Light incident on back absorber
93. Light incident on back absorber
94. Light incident on back absorber
95. Internal reflection
96. Internal reflection
97. Internal reflection FIG. 8 Cross sectional view of empty molecularly permeable membrane ampoule with super lattice Bragg reflectors 100. Back plane absorber
101. Molecular permeable membrane
102. Light reflection off layer
103. Light reflection off layer
104. Light reflection off layer
105. Incident electromagnetic light waves
106. Light observer
107. Constructive interference
108. Air in ampoule
109. Air in super lattice
110. Super lattice layer
111. Super lattice layer
112. Super lattice layer
113. Light incident on absorber
114. Light incident on absorber
115. Light incident on absorber
116. Internal reflection
117. Internal reflection
118. Internal reflection FIG. 9 Cross sectional view of scent liquid filled molecularly permeable membrane ampoule with hydrophobic textured membrane surfaces 119. Glue Joint
120. Battery electrical energy supply
121. Transmission through roughened surface
122. Molecularly permeable membrane
123. Transmission through roughened surface observed
124. Transmitted light observed
125. Optical observer
126. Scent liquid
127. Back plane light emitter
128. Electrical switch
129. Second silicone sheet FIG. 10 Cross sectional view of empty molecularly permeable membrane ampoule with hydrophobic textured membrane surfaces 130. Battery electrical energy supply
131. Molecular permeable membrane
132. Scattering off dried surface
133. Emitted photons
134. Scattered light
135. Optical observer
136. Transmitted reflected light
137. Air in the hydrophilic channel
138. Scent liquid
139. Scattered light reflected off dried hydrophobic surfaces
140. Light emitter
141. Electrical switch FIG. 11 Cross sectional view of scent liquid filled molecularly permeable membrane tubular ampoule with connector 150. Silicone molecularly permeable membrane
151. Silicon molecularly permeable membrane
152. Scent liquid
153. Barbed connector
154. Liquid scent in hydrophilic side of connector
155. Meniscus of scent fluid in hydrophobic connector reservoir
156. Connector wall
157. Air in connector on hydrophobic side
158. Air in tube
159. Meniscus of wetted scent liquid in tube FIG. 12 Cross sectional view of empty molecularly permeable membrane tubular ampoule with connector 170. Molecular permeable membrane
171. Molecular permeable membrane
172. Coalesced dyed scent liquid
173. Barbed connector
174. Hydrophilic side of connector
175. Air in connector
176. Hydrophobic wall of connector
177. Hydro phobic side of connector
178. Air molecular permeable membrane tube
179. Coalesced liquid with remaining scent and dye FIG. 13A Hydrophilic and hydrophobic patterned liquid segregation in molecular permeable membrane ampoule 190. Edge seal region
191. High surface area hydrophilic
192. Medium surface area hydrophilic
193. Low surface area hydrophilic
194. Hydrophobic surface area FIG. 13B Cross sectional view through the hydrophobic and hydrophobic gradient patterned ampoule filled with scent liquid 195. Molecular permeable membrane
196. Scent liquid
197. Bubble of air as used
198. Hydrophobic region
199. Scent liquid
200. Medium surface area hydrophilic region
201. Bond region
202. High surface area hydrophilic region
203. Impermeable barrier layer
204. Back wall material layer FIG. 13C Cross sectional view through the hydrophobic and hydrophobic gradient patterned ampoule filled with remaining scent liquid in hydrophilic corners 205. Molecular permeable membrane
206. Air bubble
207. Hydrophobic region
208. Remaining scent liquid migrated to hydrophobic region
209. Hydrophobic pores
210. Impermeable backing layer
211. Membrane back wall of ampoule FIG. 14A Cross sectional lengthwise view of molecularly permeable tubular ampoule with hydrophilic segregation of liquid to capillary channels 217. Polyester wicking thread
218. Polyester wicking thread
219. Polyester wicking thread
220. Molecular permeable tube wall
221. Scent liquid
222. Gas bubble
223. Molecular permeable tube wall FIG. 14B Cross sectional view perpendicular to molecularly permeable tube ampoule with hydrophilic capillary channel separation half full of scent liquid.

224. Small half capillary channel
225. Wall of capillary channel hydrophilic
226. Molecular permeable wall
227. Scent liquid attracted to capillary channels
228. Gas bubble FIG. 14C Cross sectional view perpendicular to the molecularly permeable tube ampoule with hydrophilic capillary channel separation of remaining scent liquid
229. Capillary channel with scent liquid
230. Remaining scent liquid in capillary channel
231. Gas bubble
232. Molecular permeable membrane wall of tube FIG. 15A Cross sectional view of porous tubular band with molecular permeable tubular membranes and viewing port
240. Bond region
241. Porous outer membrane film
242. Tubular membrane film
243. Scent liquid
244. Viewing aperture
245. Bond region
246. Porous backing layer
247. Impermeable barrier layer FIG. 15B Porous tubular band with molecular permeable tubular membranes with viewing port and button fasten system
250. Porous outer membrane film
251. Tubular ampoules
252. Aperture in porous membrane film
253. Button or barb button
254. Top porous layer
255. Impermeable layer
256. Porous bottom layer
257. Opening at end of tube to allow insertion and removal of tubular ampoules
258. Button hole
259. Button hole FIG. 16 Perforated reel cover cap and wound tubular ampoule
270. Molded cover cap and reel
271. Vent hole
272. Silicone tube ampoule
273. Center tube viewing aperture
274. First leg of reel
275. Second leg of reel
276. Molecular permeable tube ampoule crossing beneath viewing hole FIG. 17A Perforated reel cover cap with wound tubular ampoule positioned to be inserted
280. Perforated cover cap and reel
281. Center viewing aperture
282. Tubular molecularly permeable membrane
283. Reel leg
284. Vent aperture through cap FIG. 17B Slap-band to receive the perforated cap cover
290. Rubber sleeve
291. Cavity in rubber sleeve
292. Slap-band with tempered bi-stable strip encapsulated with rubber FIG. 17C Assembled second delivery system with slap-band attachment
300. Central vent and viewing aperture
301. Cavity rubber sleeve
302. Slap-band with tempered bi-stable strip encapsulated with rubber FIG. 17D Assemble mosquito repellent band inserted into a re-sealable bag
310. Zip channel bag seal
311. Low permeability polyester polyethylene laminated bag
312. Slap band
313. Bottom of bag
314. Cover cap of scent diffusion source Examples of features and elements in several embodiments of the invention include:
  Sealed ampoules of scent liquid
  Surface textured membrane walls of ampoules
  Surface textured membranes within the ampoules
  Pores or surface features smaller than 1 micron to produce scattering of light
  Light diffraction features
  Light reflective features
  Light reflective diffraction grating or hologram that when wetted or dry from scent contact produces dramatically different colors when viewed from above.
  Thin film interference filters that when surface is coated with scent liquid inhibits or enables the constructive of destructive interference of light.
  Color Reflectors
  Materials with small pores or structural features with similar index of refraction to scent liquid such that when wetted are transparent to light and when dry scatter light.
  Tubular ampoules
  Level indicator
  Interference with light
  The index of refraction effect of dry vs. wet
  Constructive interferences
  Layered super lattices
  Cartridges
  Random scattering
  Hydrophobic (fears water) will eject water. When only water left the porous material will become non-wetted.
  Hydrophilic surface will attract water.
  Reflectors
  Retro-reflectors
  Many ways to make scattering surfaces
  Make the scattering surface on the containment membrane.
  Membrane enables the indicator
  Quantum dot photoemission source
  Dye, scintillator or quantum dot source suspended in the essential oil Scintillator light source Fluorescent light source Phosphor light source Electrically powered light source Surface coating on the membrane attracts the oil Can achieve a proportionate level indicator with pre-sized exclusions wicking toward the smaller pores as the liquid level decreases.

Pores that are tapered (liquid level progresses from large pore diameter to small pore diameter)

Tubular ampoules that as they are expended have bubbles. So if the tube is tapered or has a wetting gradient then the liquid level can be progressive and act as a capacity gauge.

Grooves or channels of different sizes that preferentially attract remaining scent liquid to form appearance changes of the ampoules light reflection or transmission.

Tubular loop ampoules that shows liquid level.

Flat seal ampoule

Multiple ampoules

Tubular ampoule with connector

Re-sealable and refillable ampoules

Re-sealable and refillable tubular ampoules

Cartridge cage acts as a reel for the tubular ampoule.

Central region of reel ampoule acts as diffusion or flow pathway for tubular and flat sealed ampoule.

Cartridge cage with large hole sufficient to allow viewing of ampoules

Ampoule with material that indicates liquid or no liquid repellent present.

Liquid indicator material has porosity with pores less than 4 microns that when filled with liquid repellent will be transparent and when dry will reflect light.

The ampoule or liquid in ampoule is tinted red or pink to be attractive to mosquitos.

Color dye in the ampoule that as the scent oil is expended is more concentrated and becomes darker.

Color associated with the oil and concentration of soap or long chain molecules (hydrocarbons) that can't go through the membrane and with a solubility limit so precipitates come out and absorb light or color change.

Colloidal Oil

The eye hole is a viewing port.

The cassette has an eye hole port and reflector ampoule.

The number of hours pattern left is viewed and then obscured as the scent fluid is expended. To create a kind of count-down. (999, −99, −9)

The liquid attractant features that hold the remaining scent liquid form geometric patterns that are an indicator of fill level.

Color patterns of a circular fuel gauge.

Techniques to produce porous surfaces of irradiation and etching, porous material, sand blasting, molding, laser etching, printing, precipitation, condensation, sponge formation.

Surface tension changes to the scent fluid as the scent is expended and hydrophobic and hydrophilic regions or pores such that scent fluid and surfaces separate and give an indication of scent fluid level reduction.

Nano powders that when wet with oil scatters differently. Color change could very well be no reflection or color when wet, while brighter color when wet.

The invention claimed is:

1. An apparatus comprising a scent vapor delivery liquid reservoir containing a scent liquid, with some or all walls of the reservoir comprising a membrane that is molecular diffusion permeable to the contained scent liquid whereby the membrane emits scent vapor to surrounding air, wherein some or all of the walls of the reservoir are transparent to light, and wherein the reservoir further comprises an interior surface having a surface tension energy gradient for the scent liquid contained within the reservoir, such that when in contact with the scent liquid, the interior surface transmits incident light, and changes light reflectivity and emission when there is less liquid therein, enabling the scent liquid volume contained by the reservoir to be gauged by the light reflectivity and emission viewed outside of the reservoir.

2. The apparatus of claim 1, wherein the interior surface creates the surface tension energy gradient for the scent liquid such that when the interior surface is covered or bared by the scent liquid, light passing through or reflecting off surfaces inside of the reservoir enables viewing of the scent liquid covering part of the membrane therein, thereby enabling the scent liquid contained in the reservoir to be a progressing visual gauge as the scent liquid volume changes by the size and position or pattern of the scent liquid covering the part of the membrane inside the reservoir.

3. The apparatus of claim 1, wherein when incident light enters the reservoir and meets scent liquid wetted surfaces within the reservoir, the light passes deeper into and is absorbed by the scent liquid, or the light transmits through the reservoir and, when liquid departs from the surfaces, the light reflects and scatters from inside the membrane, changing the light reflectivity and emission from the reservoir.

4. The apparatus of claim 1, wherein when incident light enters the reservoir and meets scent liquid wetted surfaces within the reservoir, the light reflects or is absorbed by the scent liquid, and when the scent liquid departs from the surfaces, the light travels more deeply into the reservoir and reflects or scatters deeper within the membrane, changing the light reflectivity and emission from the reservoir.

5. The apparatus of claim 1, wherein the scent of the emitted vapor is an arthropod attractant, a repellent or a scent mask.

6. The apparatus of claim 1, wherein some or all of the walls of the reservoir are largely transparent to light when the walls are in contact with the scent liquid, and retroreflect or scatter light when the walls are not in contact with the scent liquid.

7. The apparatus of claim 1, wherein the interior surface interferes with light such that color changes of the transmitted or reflected light occur between when inner surfaces of the walls of the reservoir are wet or dry of the scent liquid.

8. The apparatus of claim 1, wherein the scent liquid reservoir is contained within a porous container having a window, which enables the liquid reservoir to be viewable.

9. The apparatus of claim 1, wherein the liquid reservoir is contained within a porous container having a window, and the apparatus further comprises a reflector of light behind the liquid reservoir, which enables the scent liquid in the liquid reservoir to be viewable by light reflections.

10. The apparatus of claim 1, wherein the liquid reservoir is contained within a porous container having a window, and the apparatus further comprises an absorber of light behind the liquid reservoir, which enables the scent liquid in the liquid reservoir to be viewable by light reflections from the reservoir.

11. The apparatus of claim 1, wherein the liquid reservoir is contained within a porous container having a window, and the apparatus further comprises a light source behind the reservoir, which enables the scent liquid volume in the liquid reservoir to be viewable by light emitted from the light source through the reservoir.

12. The apparatus of claim 11, wherein the light source is a light diffuser, a light reflector, an electrically stimulated light source, a phosphor, a scintillator, a fluorescer, a thermoluminescent material, a chemi-luminescent material, sunlight, an incandescent source, or a light emitting diode.

13. The apparatus of claim 1, wherein the reservoir further includes one or more additional materials therein which are porous, powdered, or faceted, and which are insoluble in the scent fluid, and the membrane walls, or the additional materials are transparent to the light with an index of refraction difference smaller than 0.06 between the scent fluid and the porous, powdered, or faceted material, or the membrane walls.

14. The apparatus of claim 1, wherein the reservoir further includes one or more inserted components, and wherein the one or more inserted components or the membrane walls include a surface treatment comprising: a texturing of the membrane walls or a texturing of surfaces of the one or more inserted components with features smaller than 4 microns, or a forming of pores in the membrane walls or the one or more inserted components smaller than 4 microns, or a coating on the membrane walls or the one or more inserted components, whereby a constructive interference is produced from liquid solid surface lattices resulting from the surface treatment, and whereby the scent fluid can access these features and change the light reflectivity and emission or the constructive interference.

15. The apparatus of claim 1, wherein the interior surface having the surface tension energy gradient is asymmetric within the liquid reservoir.

16. The apparatus of claim 1, further comprising a dye infused into the scent liquid.

17. The apparatus of claim 16, wherein the dye infused into the scent liquid is a fluorescent dye, quantum dots, a scintillator, a phosphor, a chemi-luminescent dye, or a thermo-luminescent dye.

18. The apparatus of claim 1, wherein the scent liquid further includes surfactants added thereto, whereby the scent liquid modifies the surface tension energy gradient between the scent liquid and the interior surface of the reservoir, such that the surfactants become more concentrated as the scent liquid molecularly diffuses from the reservoir, or such that the surfactants become less concentrated as the scent liquid molecularly diffuses from the reservoir.

* * * * *